US012678301B2

(12) United States Patent
Herr et al.

(10) Patent No.: US 12,678,301 B2
(45) Date of Patent: Jul. 14, 2026

(54) METHOD AND SYSTEM FOR DESIGNING A BIOMECHANICAL INTERFACE CONTACTING A BIOLOGICAL BODY SEGMENT

(71) Applicant: Massachusetts Institute of Technology, Cambridge, MA (US)

(72) Inventors: Hugh M. Herr, Somerville, MA (US); Kevin Mattheus Moerman, Lexington, MA (US); David Moinina Sengeh, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 169 days.

(21) Appl. No.: 16/069,837

(22) PCT Filed: Jan. 12, 2017

(86) PCT No.: PCT/US2017/013154
§ 371 (c)(1),
(2) Date: Jul. 12, 2018

(87) PCT Pub. No.: WO2017/123729
PCT Pub. Date: Jul. 20, 2017

(65) Prior Publication Data
US 2019/0021880 A1     Jan. 24, 2019

Related U.S. Application Data

(60) Provisional application No. 62/377,128, filed on Aug. 19, 2016, provisional application No. 62/278,158, filed on Jan. 13, 2016.

(51) Int. Cl.
*A61F 2/50*          (2006.01)
*A61F 2/60*          (2006.01)
(Continued)

(52) U.S. Cl.
CPC .............. *A61F 2/5046* (2013.01); *A61F 2/60* (2013.01); *A61F 2/78* (2013.01); *A61F 2/80* (2013.01);
(Continued)

(58) Field of Classification Search
CPC .. A61F 2/5046; A61F 2/60; A61F 2/78; A61F 2/80; A61F 2002/5049;
(Continued)

(56) References Cited

U.S. PATENT DOCUMENTS 4,735,754 A     4/1988  Buckner
5,033,291 A     7/1991  Podoloff et al.
(Continued)

FOREIGN PATENT DOCUMENTS

EP        2124764 A1     12/2009
EP       2 196 173 A2     6/2010
(Continued)

OTHER PUBLICATIONS

Lacroix D., Ramírez Patiño J.F. Finite element analysis of donning procedure of a prosthetic transfemoral socket. Ann. Biomed. Eng. 2011;39:2972-2983. doi: 10.1007/s10439-011-0389-z.—DOI—PubMed (Year: 2011).*
(Continued)

*Primary Examiner* — Renee D Chavez
*Assistant Examiner* — Pursottam Giri
(74) *Attorney, Agent, or Firm* — Hamilton, Brook, Smith & Reynolds, P.C.

(57)          ABSTRACT

A method and associated system for designing a biomechanical interface of a device contacting a biological body segment of a subject includes forming a quantitative model of the biological body segment from subject specific data, conducting a biophysical analysis, such as a finite element analysis, to thereby establish a relationship, such as a
(Continued)

functional relationship, between the quantitative model and at least one feature of the biomechanical interface contacting the biological body segment, and applying the relationship to the at least one feature of the biomechanical interface contacting the biological body segment to thereby obtain an interface design for the mechanical interface of the device. The subject-specific data can include geometry of the biological body segment and the at least one feature can be associated with physiological benefit of the biological body segment.

28 Claims, 17 Drawing Sheets

(51) Int. Cl.
| | |
|---|---|
| *A61F 2/78* | (2006.01) |
| *A61F 2/80* | (2006.01) |
| *G06F 30/20* | (2020.01) |
| *G06F 30/23* | (2020.01) |

(52) U.S. Cl.
CPC .............. *G06F 30/20* (2020.01); *G06F 30/23* (2020.01); *A61F 2002/5049* (2013.01); *A61F 2002/505* (2013.01); *A61F 2002/607* (2013.01)

(58) Field of Classification Search
CPC ......... A61F 2002/505; A61F 2002/607; G06F 30/20; G06F 30/23
See application file for complete search history.

(56) References Cited

U.S. PATENT DOCUMENTS

| | | | |
|---|---|---|---|
| 5,746,772 | A | 5/1998 | Jacobs |
| 5,993,400 | A | 11/1999 | Rincoe et al. |
| 6,585,774 | B2 | 7/2003 | Dean et al. |
| 6,804,571 | B2 | 10/2004 | Fullen et al. |
| 7,377,944 | B2 | 5/2008 | Janusson et al. |
| 8,005,651 | B2 | 8/2011 | Summit et al. |
| 8,323,353 | B1 | 12/2012 | Alley et al. |
| 8,423,167 | B2 | 4/2013 | Sanders et al. |
| 8,523,951 | B2 | 9/2013 | Kania |
| 8,551,184 | B1 | 10/2013 | Herr |
| 8,613,716 | B2 | 12/2013 | Summit et al. |
| 10,806,605 | B2 | 10/2020 | Herr et al. |
| 11,883,307 | B2 | 1/2024 | Herr et al. |
| 2002/0032485 | A1 | 3/2002 | Flam et al. |
| 2003/0216815 | A1 | 11/2003 | Christensen |
| 2004/0064195 | A1 | 4/2004 | Herr |
| 2004/0068331 | A1 | 4/2004 | Cronquist |
| 2004/0260402 | A1 | 12/2004 | Baldini et al. |
| 2005/0119777 | A1 | 6/2005 | Arbogast et al. |
| 2006/0161051 | A1 | 7/2006 | Terrill-Grisoni et al. |
| 2007/0162153 | A1 | 7/2007 | Barnes et al. |
| 2010/0161076 | A1 | 6/2010 | Parllari |
| 2010/0262054 | A1 | 10/2010 | Summit et al. |
| 2010/0268135 | A1 | 10/2010 | Summit et al. |
| 2011/0082578 | A1 | 4/2011 | Stanhope et al. |
| 2012/0173001 | A1 | 7/2012 | Caspers |
| 2012/0271433 | A1 | 10/2012 | Galea et al. |
| 2013/0166256 | A1 | 6/2013 | Wirx-Speetjens et al. |
| 2013/0282141 | A1* | 10/2013 | Herr ..................... A61F 2/5046 623/33 |
| 2014/0149082 | A1* | 5/2014 | Sanders .................... A61F 2/76 703/1 |
| 2016/0058519 | A1 | 3/2016 | Herr |
| 2016/0174945 | A1* | 6/2016 | Oh ...................... A61B 8/4405 382/131 |
| 2017/0290685 | A1 | 10/2017 | Montez et al. |
| 2017/0360578 | A1* | 12/2017 | Shin ...................... B33Y 30/00 |
| 2018/0235779 | A1 | 8/2018 | Dudding |
| 2020/0138518 | A1 | 5/2020 | Lang |
| 2021/0022891 | A1 | 1/2021 | Herr et al. |

FOREIGN PATENT DOCUMENTS

| | | |
|---|---|---|
| WO | WO 03/009787 A2 | 2/2003 |
| WO | WO 2004/016158 A2 | 2/2004 |
| WO | 2006092600 A1 | 9/2006 |
| WO | 2013142343 A1 | 9/2013 |

OTHER PUBLICATIONS

Surapureddy, R., Schönning, A., Stagon, S., & Kassab, A. (2016). Predicting pressure distribution between transfemoral prosthetic socket and residual limb using finite element analysis. International Journal of Experimental and Computational Biomechanics, 4(1), 32-48. (Year: 2014).*

Zhang, Ming, Arthur FT Mak, and V. C. Roberts. "Finite element modelling of a residual lower-limb in a prosthetic socket: a survey of the development in the first decade." Medical Engineering & Physics 20.5 (1998): 360-373. (Year: 1998).*

Silver-Thorn, Barbara, and Dudley S. Childress. "Generic, geometric finite element analysis of the transtibial residual limb and prosthetic socket." Journal of rehabilitation research and development (1997). (Year: 1997).*

Jia, Xiaohong, Ming Zhang, and Winson CC Lee. "Load transfer mechanics between trans-tibial prosthetic socket and residual limb—dynamic effects." Journal of biomechanics 37.9 (2004): 1371-1377. (Year: 2004).*

Morotti, Roberto. "Development of a Virtual Testing Laboratory for Lower Limb Prosthesis." (2014). (Year: 2014).*

Zhang, Ming, et al. "Development of a non-linear finite element modelling of the below-knee prosthetic socket interface." Medical engineering & physics 17.8 (1995): 559-566. (Year: 1995).*

Xu, Dong Hao. The Study of Bone Remodelling in an Osseointegrated Percutaneous Trans-Femoral Implant. University of Surrey (United Kingdom), 2007. (Year: 2007).*

Notification of Transmittal of the International Search Report and the Written Opinion of the International Searching Authority, or the Declaration, entitield "Method and System for Designing a Biomechanical Interface Contacting a Biological Body Segment," PCT/US2017/013154, date of mailing Jun. 19, 2017.

Herr; "Exoskeletons and orthoses: classification, design challenges and future directions." Journal of neuroengineering and rehabilitation 6, No. 21 (Jun. 2009): pp. 1-9.

Morotti; "Development of a Virtual Testing Laboratory for Lower Limb Prosthesis;" Thesis, Universita degli Studi di Padova, 133 pages, (2014).

International Preliminary Report on Patentability, PCT/US2017/013154, "Method and System for Designing a Biomechanical Interface Contacting a Biological Body Segment,", date of mailing Jul. 26, 2018.

Charalambides, et al.; "A Novel All-Elastomer MEMS Tactile Sensor for High Dynamic Range Shear and Normal Force Sensing," J. Micromech. Microeng. 25(9): (9 pages) (Aug. 2015).

Dagdeviren, et al.; "Conformal Piezoelectric Systems for Clinical and Experimental Characterization of Soft Tissue Biomechanics," Nature Materials, 14, pp. 728-736 (Jul. 2015).

Invitation to Pay Additional Fees from International Application No. PCT/US2017/013154, "Method And System For Designing A Biomechanical Interface Contacting a Biological Body Segment," mailed Apr. 19, 2017.

Zheng, et al., State-of-the-Art Methods for Geometric and Biomechanical Assessments of Residual Limbs: A Review, Journal of Rehabilitation Research and Development vol. 38 No. 5, 24 pages (2001).

Gabbiadini S., "Knowledge-Based Design of Lower Limb Prosthesis," Ph.D. Thesis, Industrial Engineering. University of Padova, Italy, See http://paduaresearch.cab.unipd.it/3771/, 181 pages (2011).

Faustini, M.C., et al., "An Experimental and Theoretical Framework for Manufacturing Prosthetic Sockets for Transtibial Amputees," Neural Systems and Rehabilitation Engineering, IEEE Transactions on , vol. 14, No. 3, pp. 304-310 (2006).

Silver-Thorn, M.B, et al., "A review of prosthetic interface stress investigations," J Rehabil Res Dev ;33(3) :pp253-66 (1996).

(56) References Cited

OTHER PUBLICATIONS

Gao, F.,et al., "Finite Element Analysis Based Design Optimization for Prosthetic Socket," Annual Meeting of the American Society of Biomechanics, 2 pages (2009).

Marreiros, S., "Skin Strain Field Analysis of the Human Ankle Joint," MS Thesis, University of Lisbon, 93 pages (2010).

Liu, G. R., et al., "Smoothed Finite Element Methods," Chapter 3, CRC Press, pp. 31-82 (2010).

Colombo, G., et al. "A New Design Paradigm for the Development of Custom-Fit Soft Sockets for Lower Limb Prostheses," Computers in Industry 61, No. 6: 513-523 (2010).

Rosen, J., et al., "Modeling the Human Body/Seat System in a Vibration Environment," Journal of Biomechanical Eengineering 125, No. 2: 223-231 (2003).

Tonuk, E., et al., "Nonlinear Viscoelastic Material Property Estimation of Lower Extremity Residual Limb Tissues," Journal of Biomechanical Engineering 126, No. 2: 289-300 (2004).

Kerem Usu, "Identification of Soft Tissue Mechanical Material Model and Corresponding Parameters From In Vivo Experimental Data by Using Inverse Finite Element Method," PhD. Diss., Middle East Technical University (2008).

Moes, C., "Advanced Human Body Modelling to Support Designing Products for Physical Interaction," TU Delft, Delft University of Technology (2004).

Goh, J. C. H., et al., "Development of an Integrated CAD-FEA Process for Below-Knee Prosthetic Sockets." Clinical Biomechanics 20, No. 6: 623-629 (2005).

Rogers, B., et al. "Case Report: Variably Compliant Transtibial Prosthetic Socket Fabricated Using Solid Freeform Fabrication." JPO: Journal of Prosthetics and Orthotics 20, No. 1: 1-7 (2008).

Vannah, et al.; "Indentor Tests and Finite Element Modeling of Bulk Muscular Tissue In Vivo," J. Rehab. Res. Dev., 33(3): 239-252 (1996).

Rogers, B., et al., "Clinical Evaluation of Prosthetic Sockets Manufactured by Selective Laser Sintering", Proc. 12th Solid Freeform Fabrication Symp., pp. 505-512, 2001.

Kevin M. Moerman et al., "Automated and Data-driven Computational Design of Patient-Specific Biomechanical Interfaces" (Year: 2016).

Lee, W.C., Zhang, M. Mak, A. F. (2005) "Regional differences in pain threshold and tolerance of the transtibial residual limb: including the effects of age and interface material," Archives of Physical Medicine and Rehabilitation, 86 (4), 641-649.

David M. Sengeh et al.; "Multi-material 3-D viscoelastic model of a transtibial residuum from in-vivo indentation and MRI data"; Journal of the Mechanical Behavior of Biomedical Materials 59 (2016) 379-392 (Year: 2016).

Ch Itresh Nayak, Customized Design and Development of Transtibial Prosthetic Socket for Improved Comfort Using Reverse u Engineering & Additive Manufacturing, Thesis submitted as a partial fulfillment of the requirements of the degree of Doctor of Philosophy; (Year: 2017), 200 pp.

Erdal Ozbay et al., Structured Deep Learning Supported with Point Cloud for 3D Human Pose Estimation, ISMSIT 2017 1st International Symposium on Multidisciplinary Studies and Innovative Technologies;2017, 6 pp.

U.S. Final Office Action for U.S. Appl. No. 16/969,142, entitled "Quantitative Design and Manufacturing Framework for a Biomechanical Interface Contacting a Biological Body Segment", mailed on Jul. 22, 2024, 51 pp.

U.S. Non-Final Office Action for U.S. Appl. No. 16/969,142, entitled "Quantitative Design and Manufacturing Framework for a Biomechanical Interface Contacting a Biological Body Segment", mailed on Dec. 14, 2023, 57 pp.

U.S. Non-Final Office Action for U.S. Appl. No. 16/969,142, entitled "Quantitative Design and Manufacturing Framework for a Biomechanical Interface Contacting a Biological Body Segment", mailed on Jan. 28, 2025, 58 pp.

* cited by examiner

Virtual test
socket
optimization

Patellar ligament

Patella

Femur

Fibula

Tibia

Skin

Design Strategy 1

Design Strategy 2

Design Strategy 3

Design Strategy 4

0    2    4    6    8    10    12    14    16    18

Sleeve

Sockets

Foot/ankle system

Front     Right     Back

Design Strategy 1

Design Strategy 2

Design Strategy 3

Design Strategy 4

-100  -90  -80  -70  -60  -50  -40  -30  -20  -10  0

Middle right  Middle front  Fibula front

Design Strategy 1

Design Strategy 2

Design Strategy 3

Design Strategy 4

0    0.1    0.2    0.3    0.4    0.5

METHOD AND SYSTEM FOR DESIGNING A BIOMECHANICAL INTERFACE CONTACTING A BIOLOGICAL BODY SEGMENT

RELATED APPLICATIONS

This application is the U.S. National Stage of International Application No. PCT/US2017/013154, filed Jan. 12, 2017, which designates the U.S., published in English, and claims the benefit of U.S. Provisional Application No. 62/278,158, filed on Jan. 13, 2016 and U.S. Provisional Application No. 62/377,128, filed on Aug. 19, 2016. The entire teachings of the above applications are incorporated herein by reference.

BACKGROUND

The success of technology such as ergonomic grips, form-fitting garments (e.g. shoes and bras), support structures (e.g. seating, wheelchair padding, mattresses, and cushions), wearable devices (e.g. glasses, hearing aids, watches), exoskeletons, orthopedic devices (orthopedic braces, bands and supports), and prosthetic devices (e.g. upper and lower limb prostheses), relies on the presence of a high-quality biomechanical interface. Typically, biomechanical interfaces achieve appropriate load transfer through artisanal modification of interface shape. In many cases the shape of the interface resembles that of the tissue region but may deviate from it, e.g., to provide a particular fit to enhance or relieve loading. As such, the optimization of the interface is complex as it consists of the determination of the appropriate interface geometry and mechanical properties given the geometry and mechanical properties of the local tissue for which the device is designed to interface.

In the United States, over half a million people live with lower limb loss [1] and 130,000 lower extremity amputations (LEAs) are carried out annually [2]. The lifetime healthcare cost after LEA is estimated to be $649,953 [3], and the U.S. Veterans Affairs estimates LEA to account for more than $250 million in direct expenditures each year, not including civilian cases [4]. In order to restore stable and independent ambulation, and improve the quality of life for persons with LEA, advanced prosthetic foot/ankle devices have been proposed (e.g. [5]). However, a critical factor in the success of the prostheses is the connection to the human body formed by the biomechanical interface system. For transtibial amputees, this typically consists of a prosthetic liner and socket (FIG. 1), which together aim to provide stability, comfort and appropriate load distribution. A prosthetic liner is a soft sock-like layer which fits tightly around the residual limb. Despite variations in subject geometries and tissue conditions prosthetic liners are generally not subject-specific. Instead a particular size and design is simply chosen from a range of commercially available liners. Although prosthetic sockets are subject-specific, their design and manufacturing process (FIGS. 2A-2E) is presently a largely artisan procedure (see also [6],[7]). The source of the socket geometry is obtained by wrapping a cast around the residual limb of the subject. A derived positive mold is then modified with the aim to remove load from regions that are deemed vulnerable while enhancing load at regions that are deemed safe. These regions are identified using manual palpation. Finally, a test socket is manufactured from the adjusted mold for evaluation with the subject. The adjustment and test socket evaluation process is then repeated until the subject can tolerate the loads on their limb, after which a final socket is manufactured. The success of this traditional socket design process relies heavily on the experience of a prosthetist, and requires manual and iterative design evaluation demanding repeated subject feedback.

The manual nature of the process means it is not strongly repeatable and currently largely non-data-driven, and quantitative data is either not obtained or insufficiently employed. As such there is a reported discrepancy in the quality of sockets produced by prosthetists [8]. Furthermore, it has been reported that 57% of lower extremity prosthetic users experience moderate to severe pain when wearing their device [9]. Discomfort commonly results in skin problems and tissue damage (e.g. [10]-[13]). In severe cases when loading conditions cause tissue deformation thresholds to be exceeded (see also [14] on thresholds), painful pressure ulcers may occur [15]; in some reports pressure ulcers have occurred in as high as 55% of subjects with major amputations [16]. However, even mild discomfort may be concerning as it could result in an altered posture and gait, which in turn may cause long term musculoskeletal conditions such as back pain [17]. Moreover, any limitation in mobility can further contribute to conditions such as obesity, musculoskeletal pathologies including osteoarthritis, osteopenia, and osteoporosis, as well as cardiovascular disease ([3], [17], [18]).

Besides optimization of shape in prosthetic design the use of compliance may also add to comfort. For the design of comfortable shoes and footwear compliant materials have been an obvious choice. However, given that, in contrast to the human foot, the tissues of the residual limb are unevolved for loadbearing, it is surprising that for prosthetic interfaces, rigid materials (with respect to the soft tissue) have predominantly been explored. Some researchers however, have proposed compliant socket designs to offer relief in vulnerable regions, such as near bony protrusions. For instance by varying the socket wall thickness and by introducing deformable structures [19], by introducing a variable spacing between a flexible inner and rigid outer socket [20], and finally by spatially varying the elastic material properties of the socket [21]. The preliminary findings of the latter study were reduced contact pressures for a compliant socket compared to a conventional socket.

Advancements in the design and manufacturing process of sockets have been proposed. For instance, through the incorporation of computer-aided design (CAD) (e.g. commercial software [22]-[25]) and computer-aided manufacturing (CAM) technologies (see for instance [19], [21], [26], [27]). However, at present, these tools do not inform the design in a data-driven sense [28] since the actual design process remains a manual and experience based procedure. This may explain the reported preferential indifference among subjects who used both a socket made using conventional and CAD/CAM techniques [29], and that design errors remain prevalent [30]. Further, non-invasive imaging has been used to study the geometry of the residual limb, e.g. based on magnetic resonance imaging (MRI) [31][32] and ultrasound [33]. Some have proposed frameworks for socket design and evaluation based on non-invasive imaging and computational modeling. For instance, Papaioannou et al. 2011 [34] presents the use of dynamic roentgen stereogrammetry combined with image based modeling and FEA. Colombo et al. 2013 [32] and subsequent studies by the same group [35], [36] present the most detailed subject-specific socket design and evaluation framework to date. Although subject-specific geometries are derived from MRI, the socket designs are created in a computer aided but manual fashion based on experience and a-priori knowledge of manually inspected vulnerable and load-bearing regions. In addition, the above has been combined with FEA based socket design evaluation [37], [38], and socket evaluation using FEA (i.e. solely evaluation without computational design) is also presented in [39]-[41]. However, in all of these cases the soft tissue material behavior was modeled using linear elasticity which is not appropriate for analysis of large deformations. In addition, linear elasticity does not consider deformation induced stiffness enhancement due to the non-linear elastic nature of soft tissue.

Modeling of functional use often simply consists of the application of force (e.g. [19]) or displacement (e.g. [42]) boundary conditions (e.g. resulting in loading equivalent to supporting body weight). However, representation of the liner and socket induced pre-loading due to donning is far less trivial. Since the equilibrium shapes of the liner and socket do not match the undeformed soft tissue they create significant pre-strain and pre-stress. The associated large deformations also alter material stiffness and are capable of perturbing the degree of anisotropy due to the non-linear elastic properties of the soft tissue. The same may hold for the liner and socket materials if non-linear elastic materials are employed. Some researchers have attempted to account for socket donning induced pre-loads using prescribed (radial) displacements (e.g. [43]). However, these displacements likely create unnatural deformations since in reality the materials may displace not only normal but also tangential to each other. Faustini et al. [44] did not simulate pre-loading but aimed to account for deformation induced stiffness changes (due to tissue non-linear elasticity) by increasing the linear elastic stiffness in the undeformed geometry at the patellar ligament. However, with this approach the tissue remains undeformed and stress and strain free which is not realistic. Socket pre-loading effects have also been simulated by resolving socket-tissue overlap after placement using contact algorithms (e.g. [45]). Others have simulated a more complete donning process by using contact algorithms and simulation of gradual insertion of the limb inside the socket (e.g.[37], [46]. The approaches involving contact algorithms are more realistic than the use of prescribed displacements since the tissue is free to displace relative (including tangential) to the socket surface. However, contact simulations, combined with non-linear analysis, for such large relative motions are computationally intensive, especially if both the socket and tissue are deformable. In addition, even for the gradual insertion approach, the results may vary depending on the contact algorithm, the assumed friction conditions, and, most importantly, on the exact motion path of the limb. Rather than a gradual insertion, in reality the subject might push their limb inside the socket and move the limb in various directions to "settle" their limb inside the socket. Such settling motions might remove and alter tangential forces that develop during the initial large motion of the insertion. Hence there is no consensus as to what motion history to simulate for these donning simulations. In addition, for each of these studies the socket material stiffness was several orders of magnitudes higher than the soft tissue. Hence the sockets encounter no or minimal deformations during the simulated donning or loading process.

4

Figure 1:
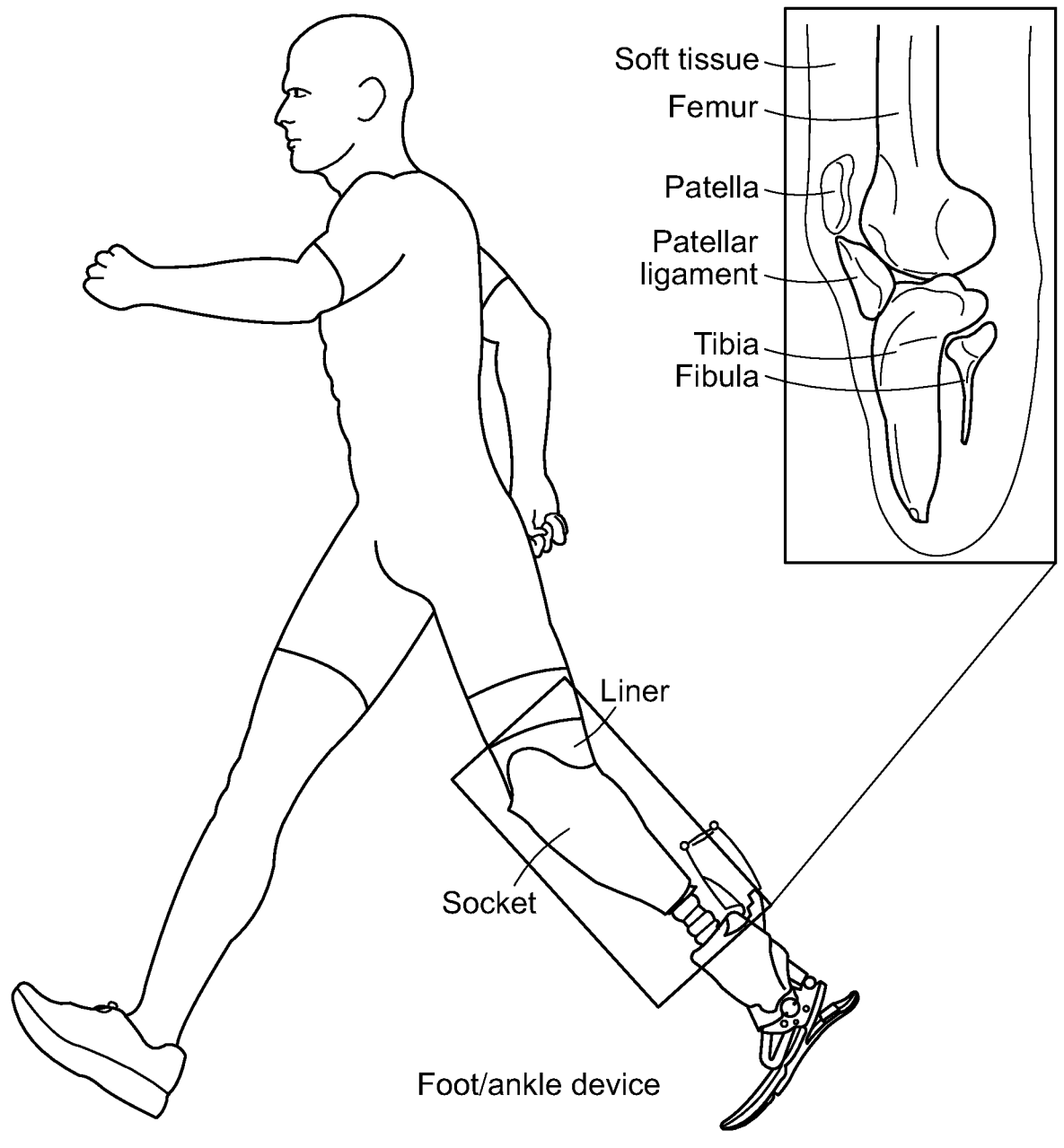
FIG. 1 shows the biomechanical interface for transtibial amputees. Schematic of main tissue structures (right) and the liner and socket system (left) (modified from [5] with permission).
Figure 2A:
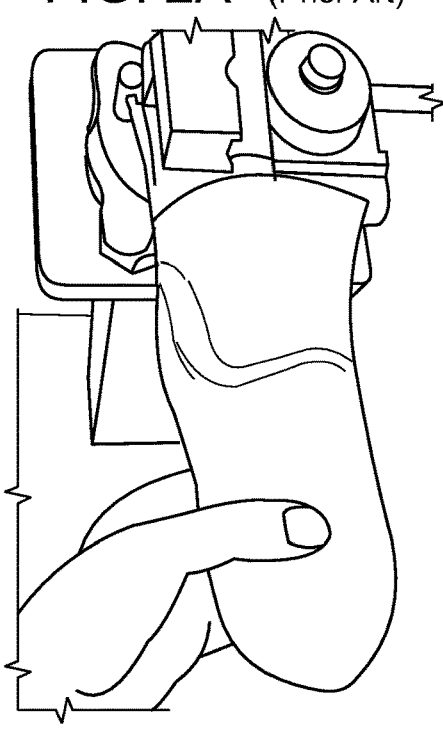
Figure 2B:
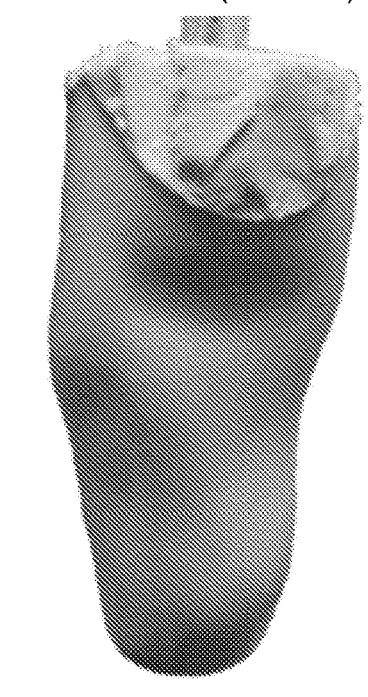
Figure 2C:
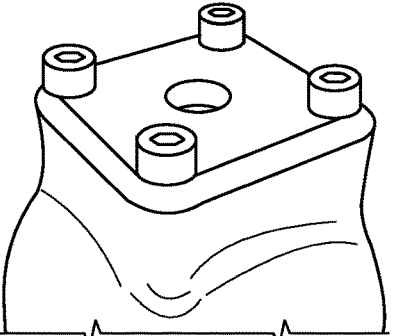
Figure 2E:
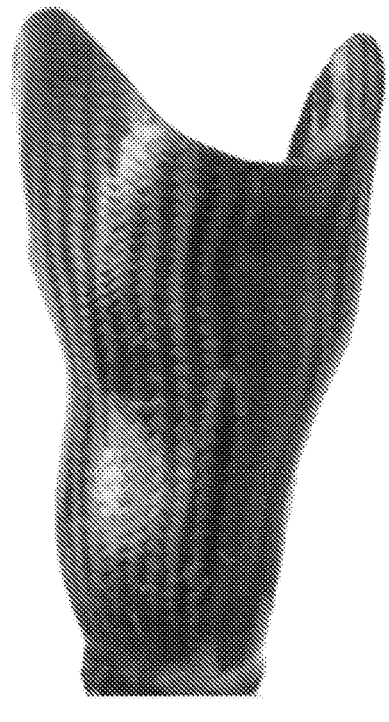
Figure 2D:
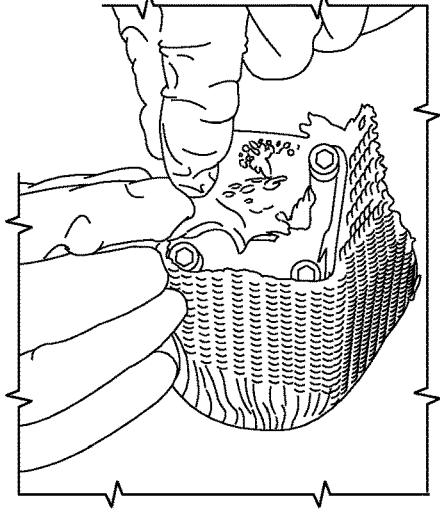

FIGS. 2A-2E show the typical traditional artisan methods for prosthetic socket design. A plaster cast mold is created for the residual limb, and cut lines are manually defined (FIG. 2A), the mold shape is then manually adjusted to define the socket inner shape (FIG. 2B), after the vertical axis is determined an attachment plate is mounted (FIG. 2C), next carbon fiber layers are wrapped over the mold (FIG. 2D) to produce the final socket design (FIG. 2E).

Figures 3A, 3B, 3C, 3D, 3E, 3F, 3G, 3H, 3I, 3J, 3K:
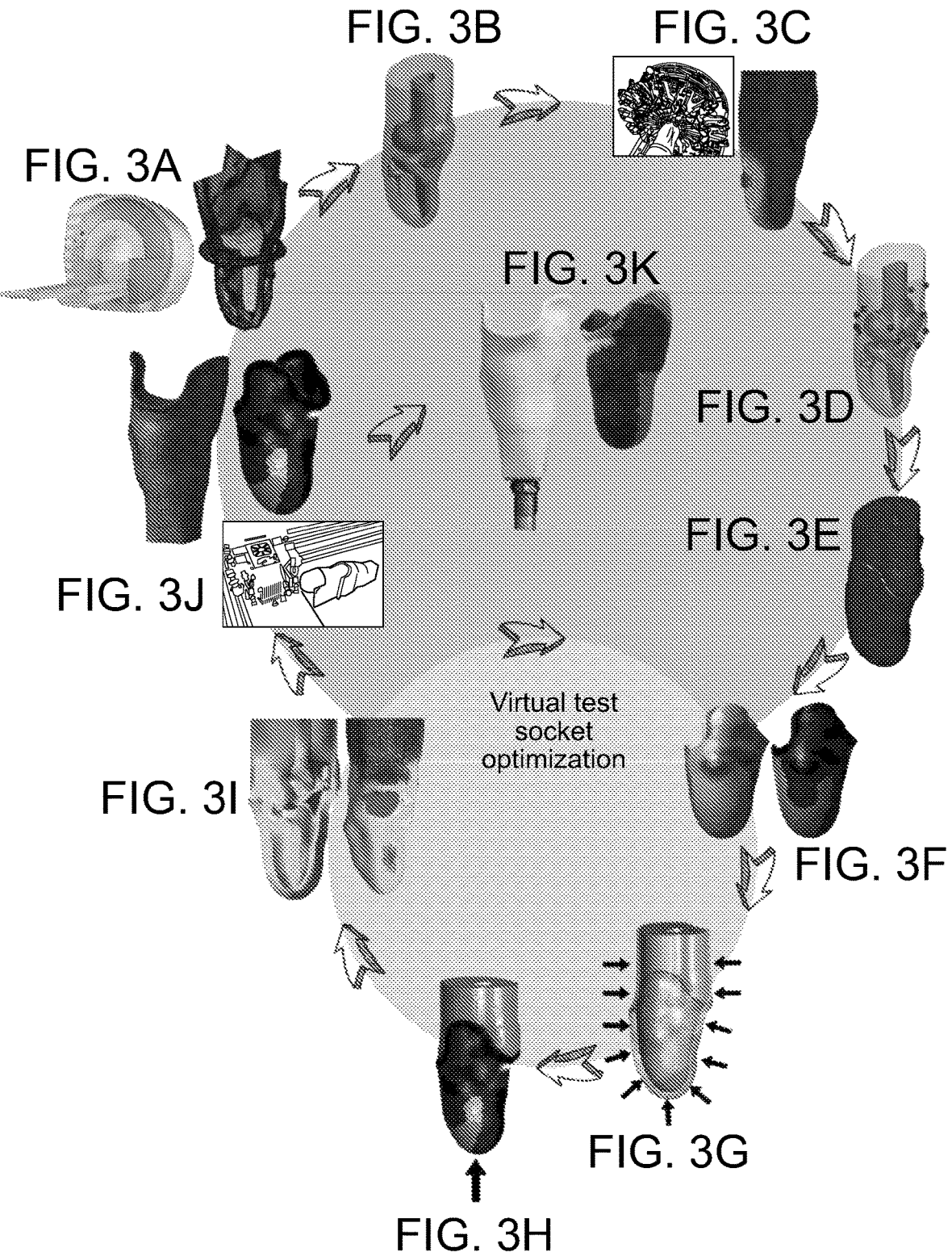

FIGS. 3A-3K provide an overview of an embodiment of a data-driven computational design framework. By segmenting Mill data (FIG. 3A), the subject-specific geometry is obtained (FIG. 3B). Indentation tests and inverse FEA can be used to determine the subject-specific tissue mechanical properties (FIG. 3C). Using anatomical landmarks the socket cut-lines can be automatically created (FIG. 3D), the liner and socket source geometries can be offset from the skin surface and can be meshed with the soft tissue to form a single FEA model (FIG. 3E), spatially varying socket stiffness and local fitting pressures can be defined (FIG. 3F), allowing for the morphing of the socket into a desired shape, while also pre-loading the tissue due to donning (FIG. 3G), the designs can now be evaluated for body weight loading (FIG. 3H), enabling skin surface pressure and internal strain analysis (FIG. 3I). The process FIG. 3F-I can be iteratively repeated and optimal designs can be exported for 3D printing based manufacturing (FIG. 3J), of the compliant inner and rigid outer socket (FIG. 3K).

Figures 4A, 4B, 4C, 4D:
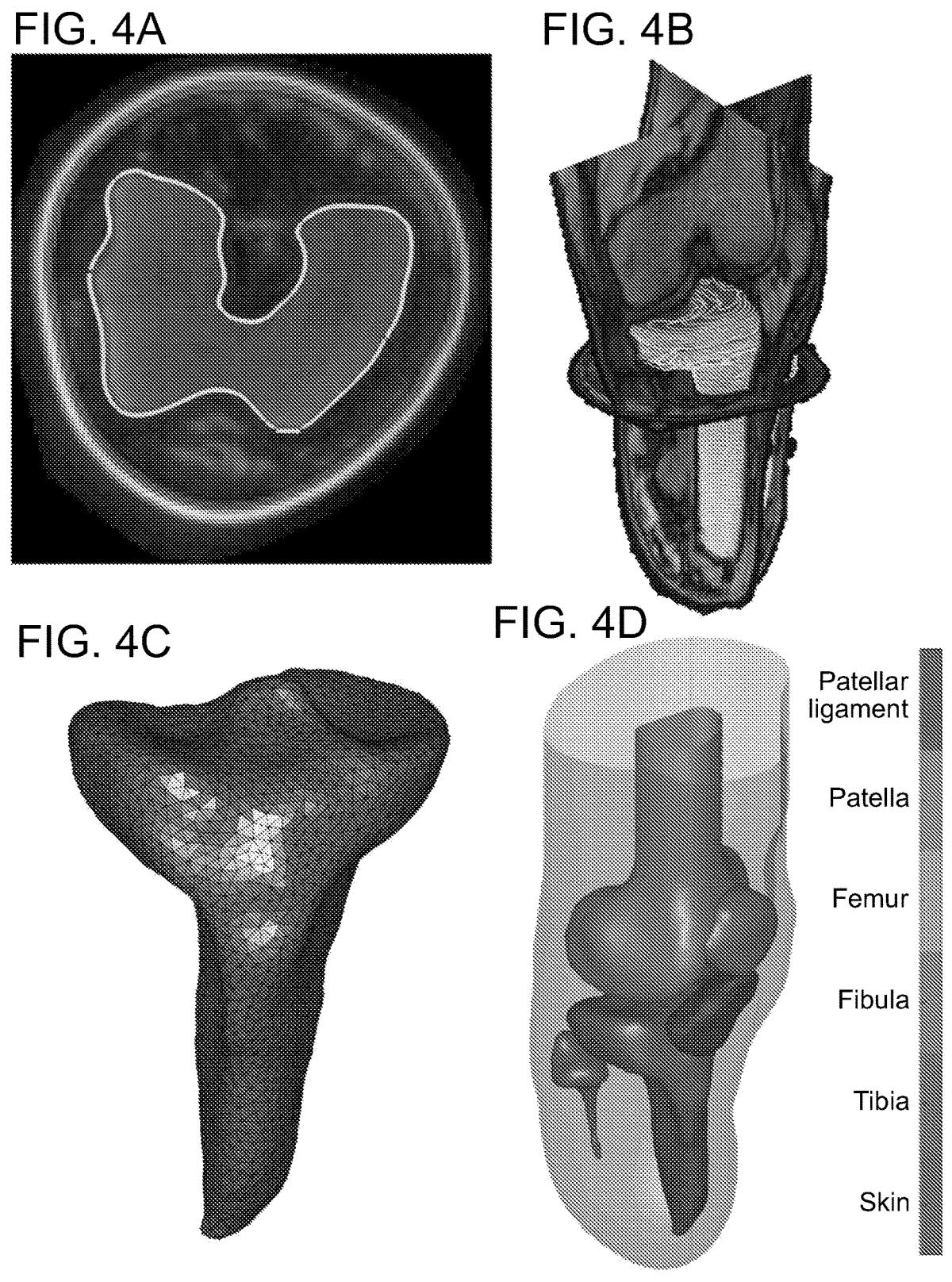

FIGS. 4A-4D illustrate the process of obtaining subject-specific body segment geometries. Tissue contours are detected for each slice of the 3D MRI data (green lines in FIG. 4A and FIG. 4B are tibia contours). Contours can be converted to surface models (C) for all tissue types (D).

Figure 5A:
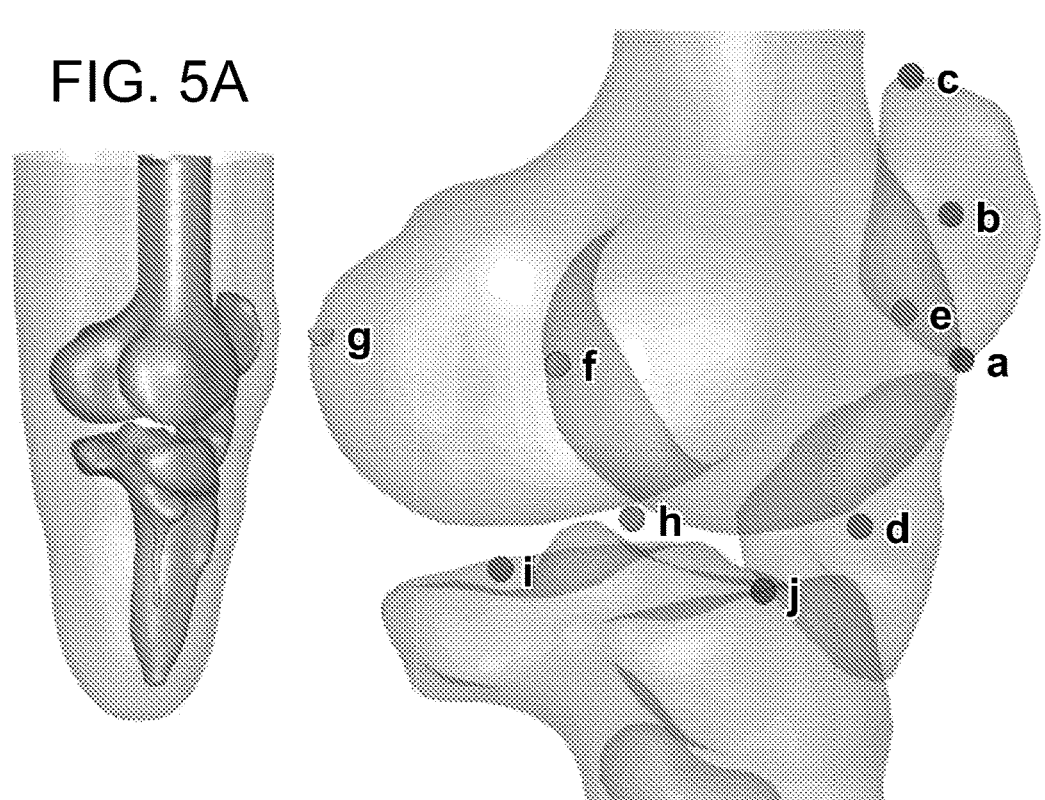
Figure 5B:
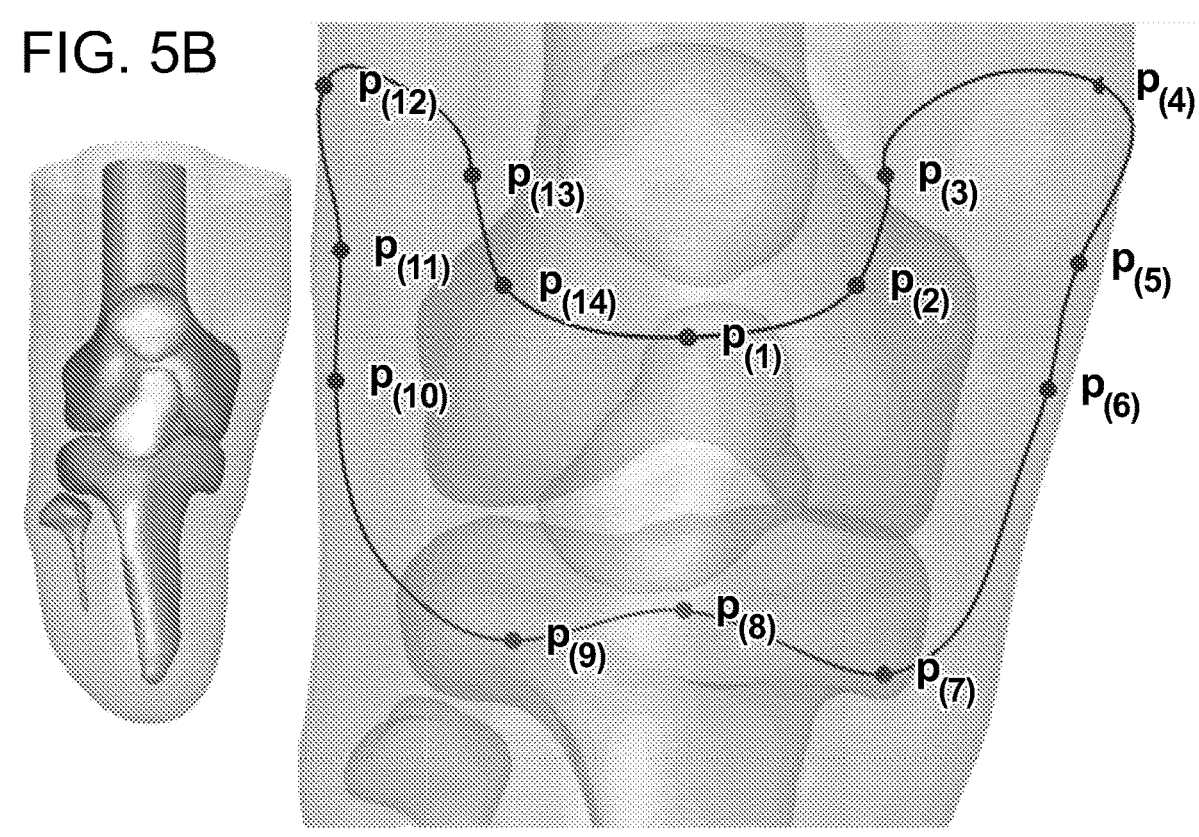
Figure 5C:
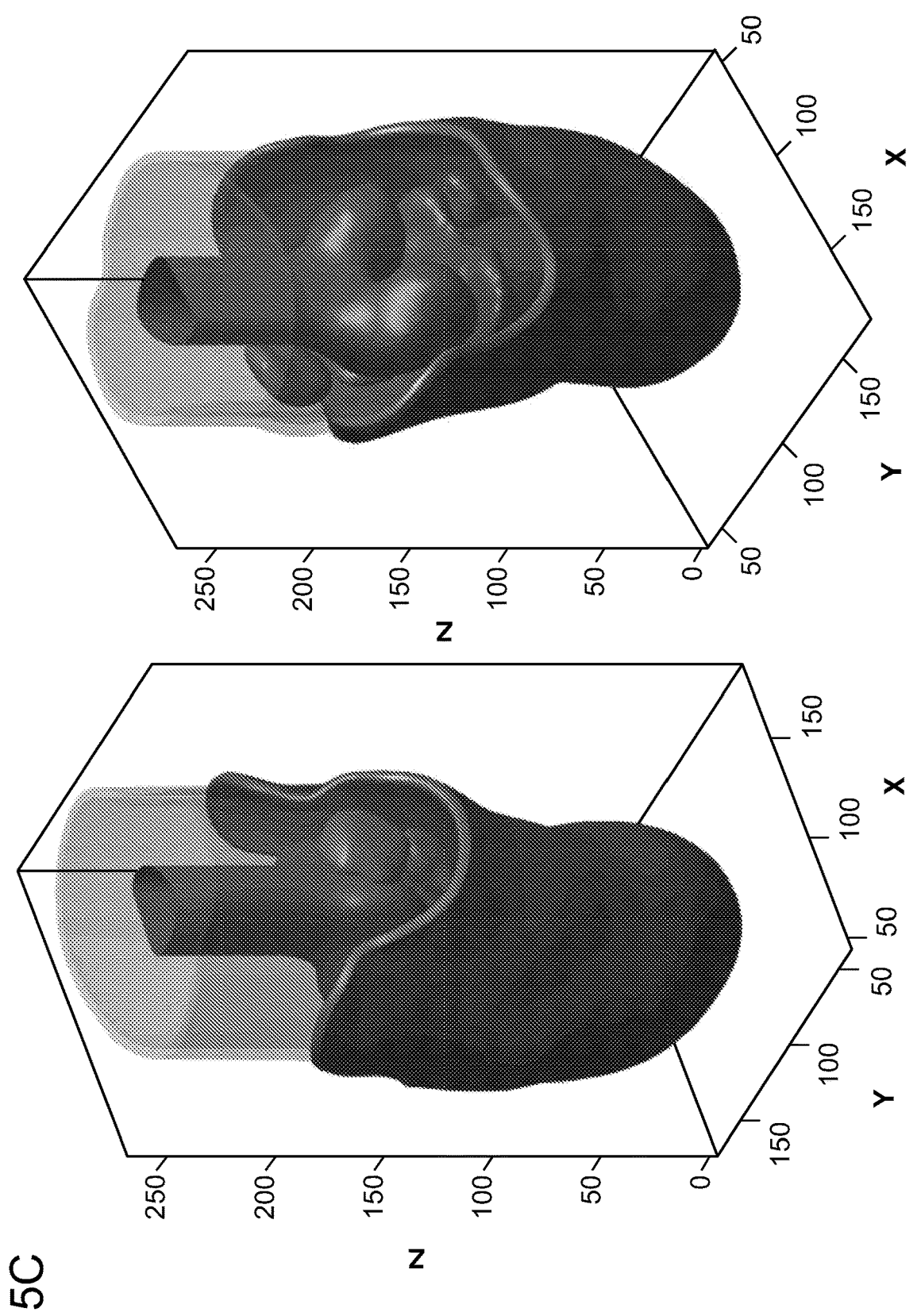

FIGS. 5A-5C illustrate the definition of the socket source geometry. The cut-line geometry is constructed based on the anatomical landmarks, shows as colored dots (FIG. 5A), through which a smooth curve can be fitted (FIG. 5B). The source geometry for the socket is then formed by offsetting the region found under the curve by a desired thickness (FIG. 5C).

Figures 6A, 6B, 6C:
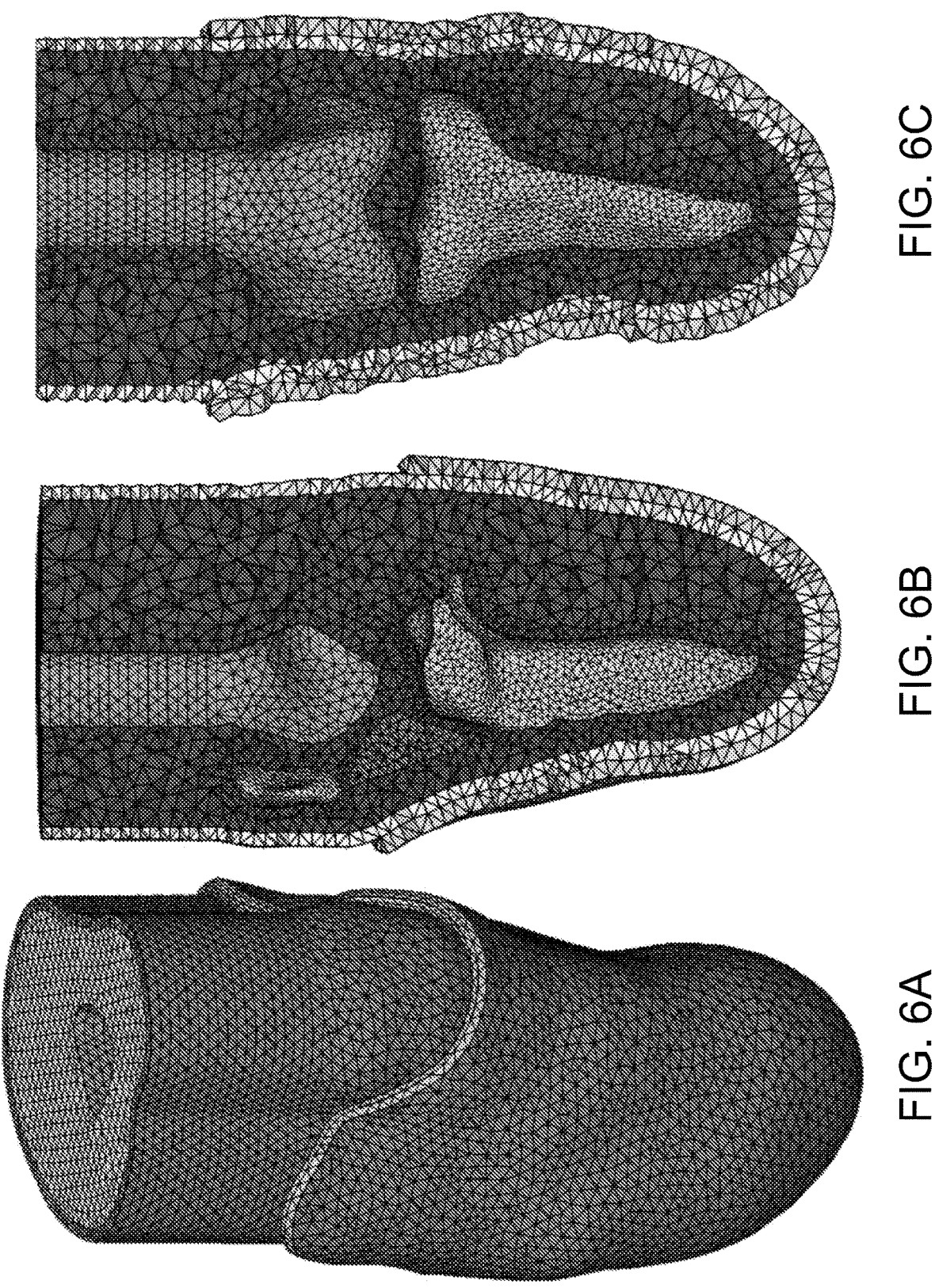

FIGS. 6A-6C illustrate a typical solid tetrahedral mesh of the residuum, liner and socket. A 3D view (FIG. 6A) and two cut views (FIGS. 6B, 6C) are shown.

Figure 7A:
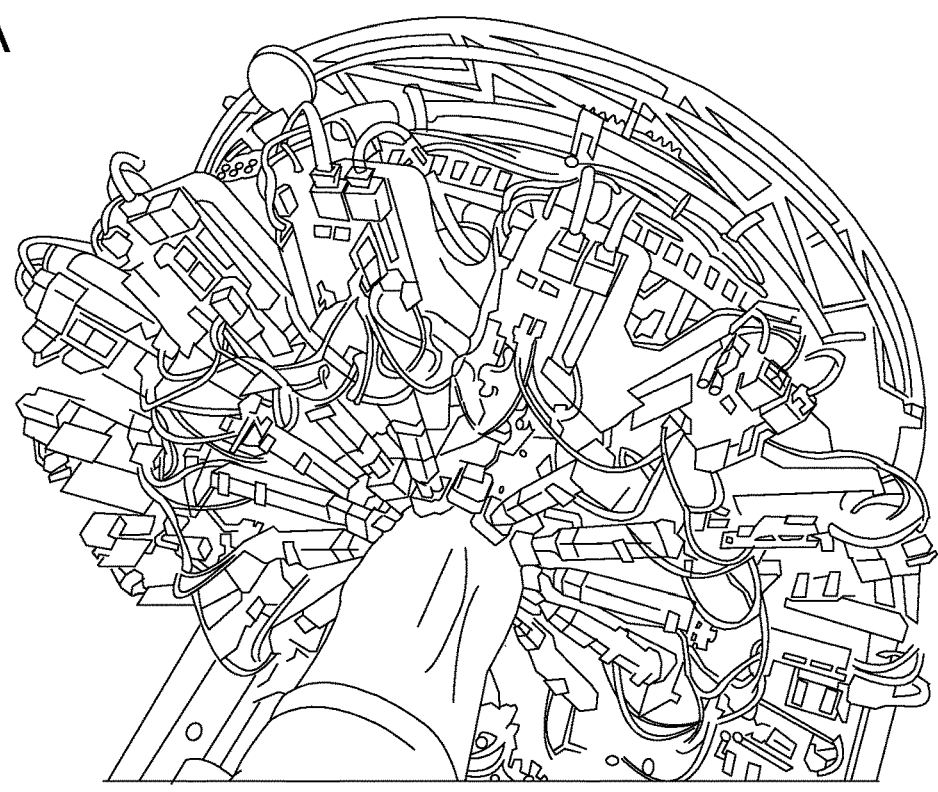
Figure 7B:
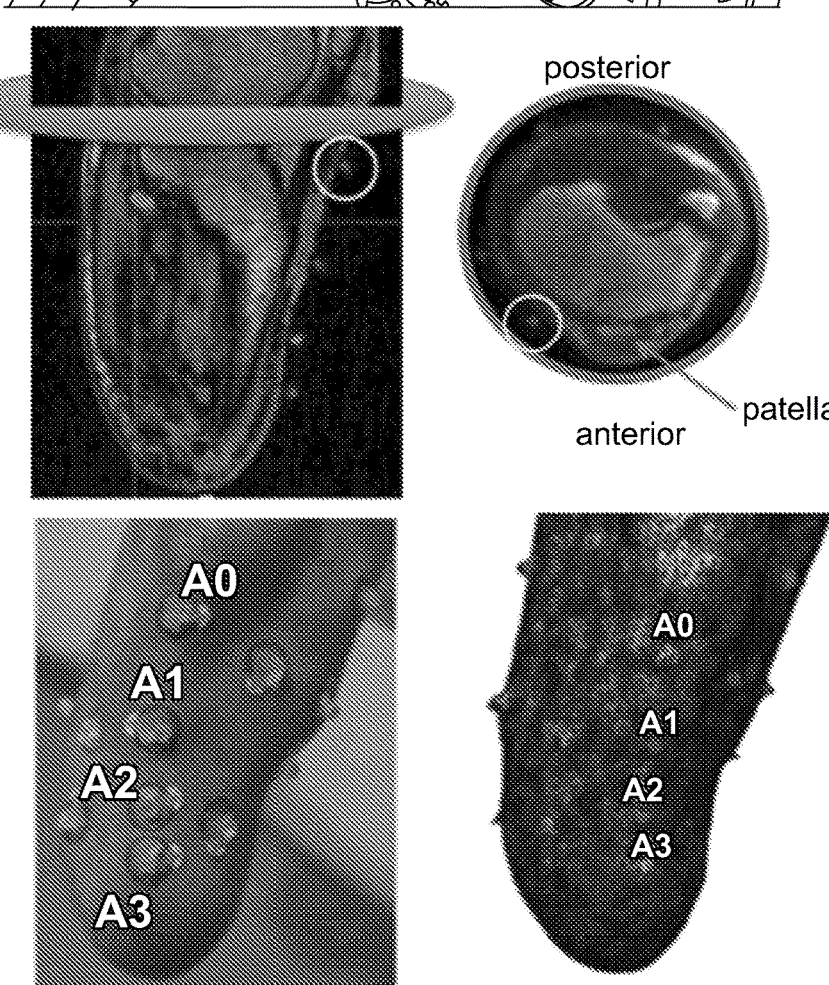
Figures 7C, 7D:
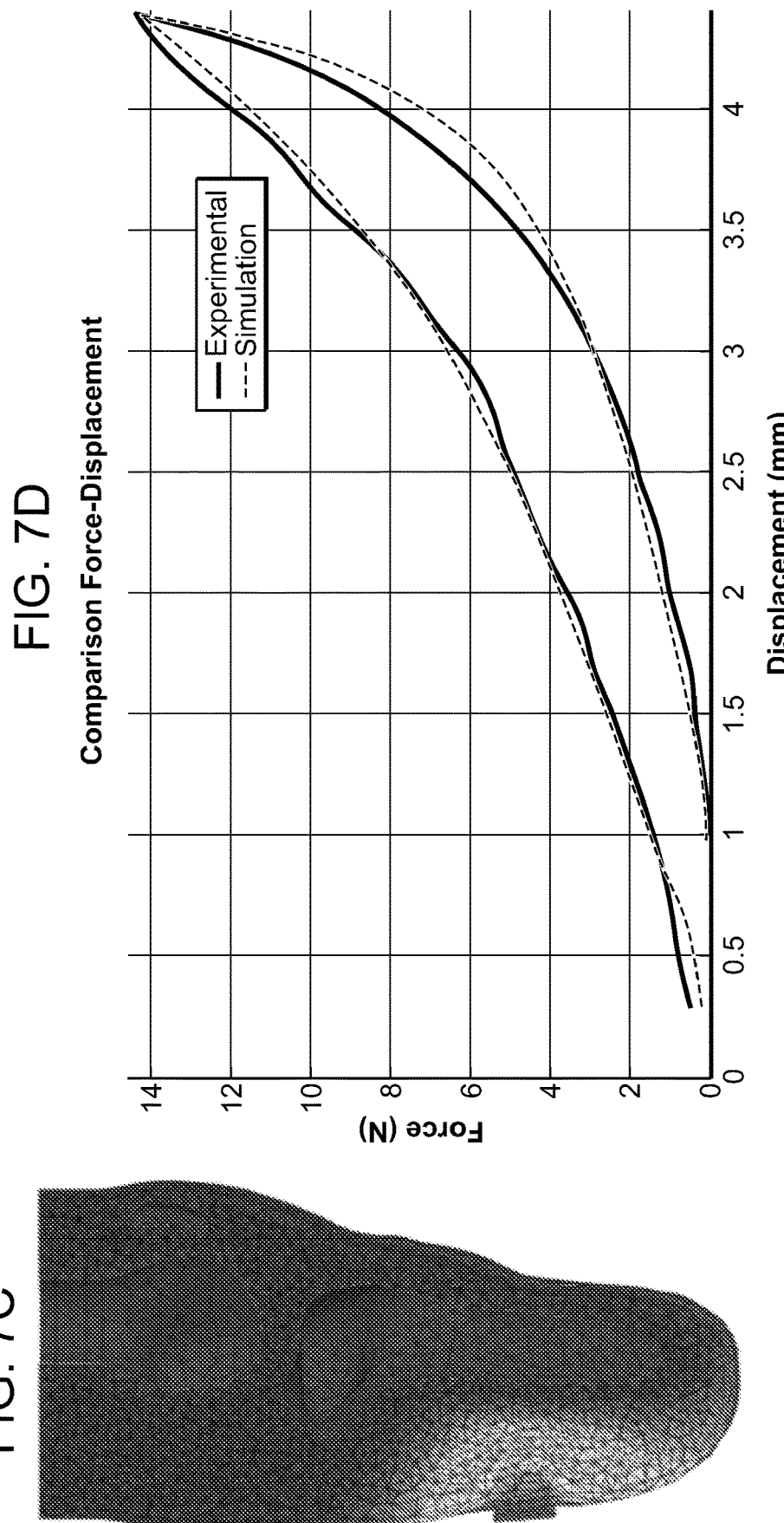

FIGS. 7A-7D Illustrates the inverse FEA based subject biomechanical property assessment process. The indentation experiment (FIG. 7A), MM markers for indentation site identification (FIG. 7B), and the Mill derived FEA model and indentation simulation (FIG. 7C) for derivation of constitutive parameters based on optimization of the force displacement response (FIG. 7D).

Figures 8A, 8B, 8C, 8D, 8E:
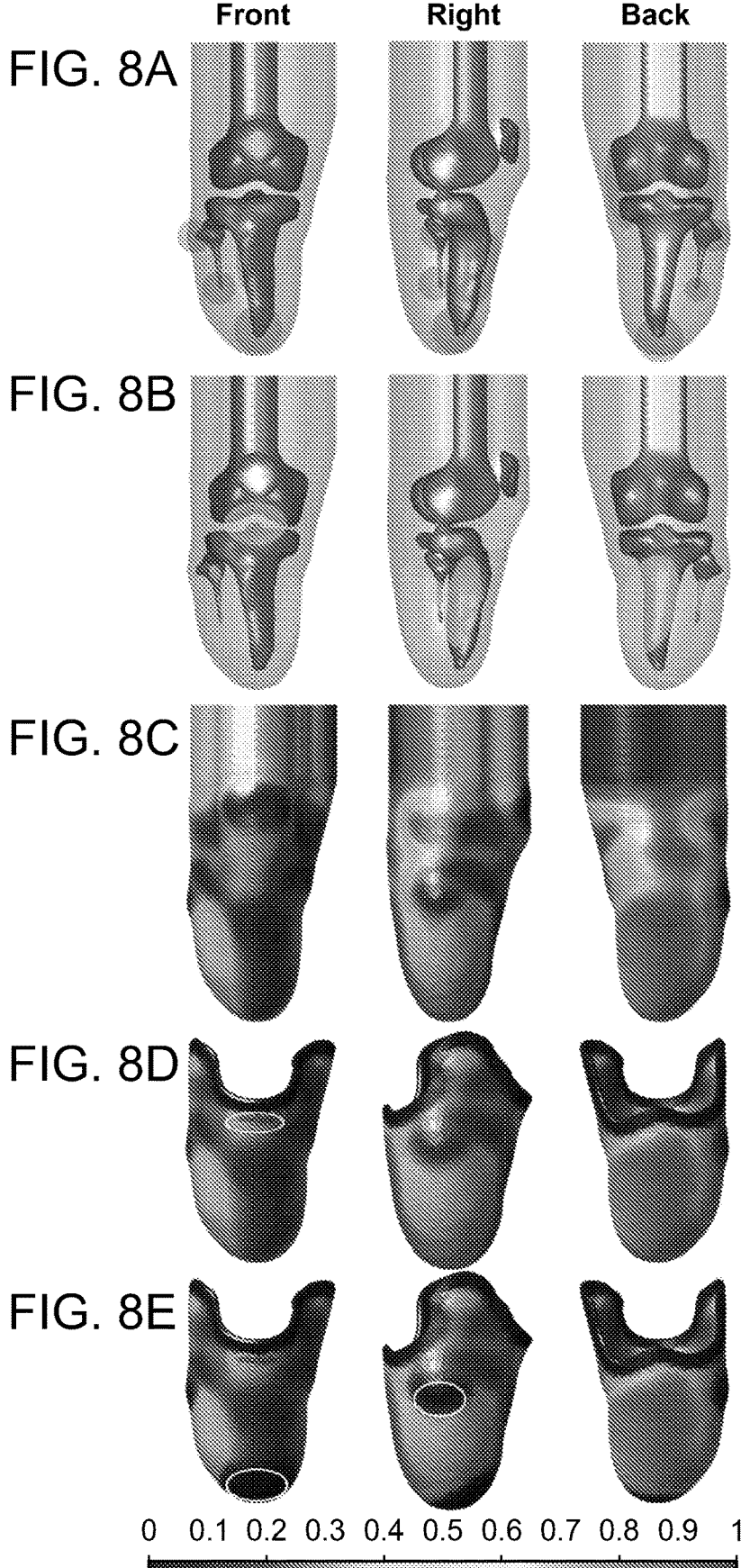
Figures 9A, 9B, 9C, 9D:
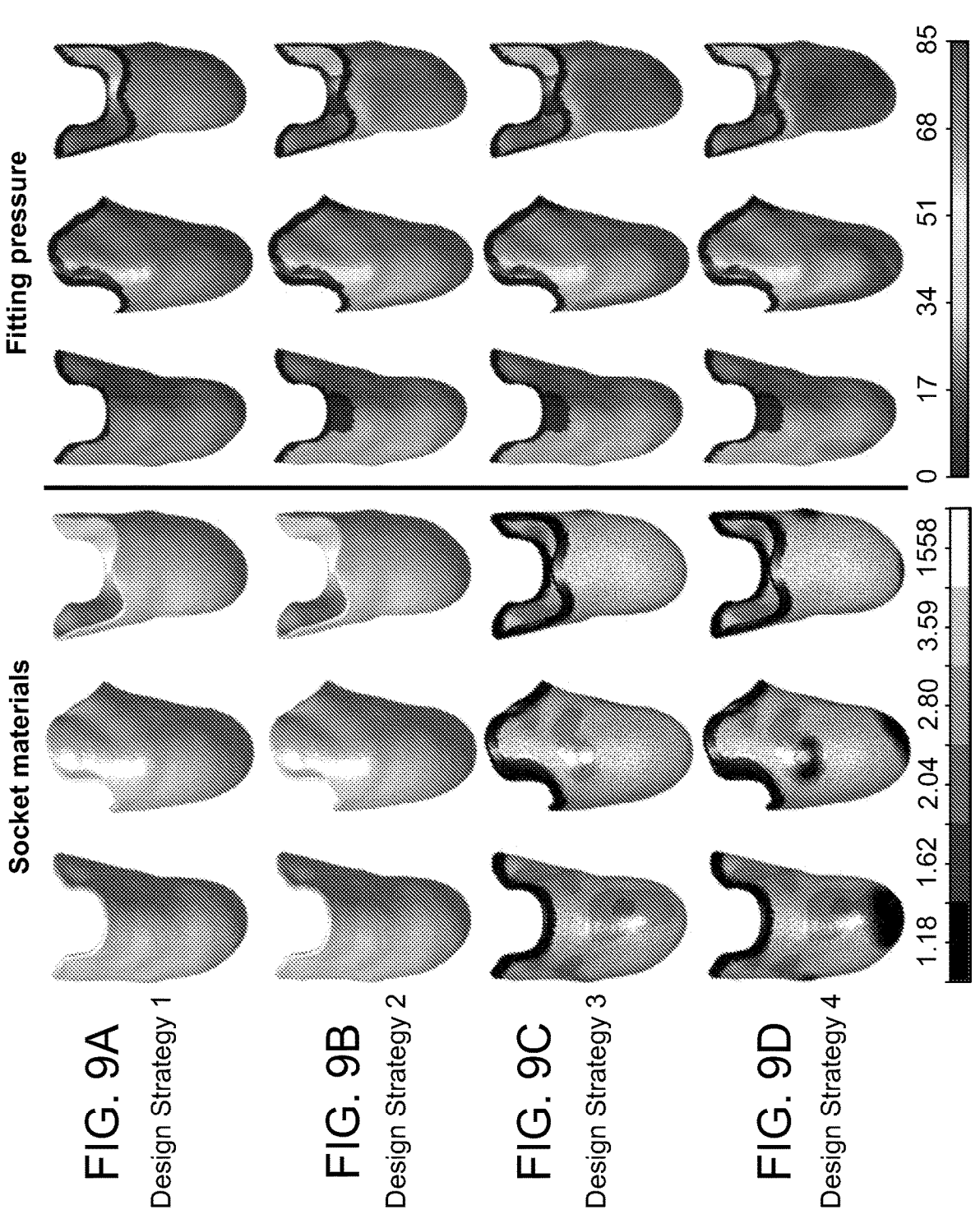

FIGS. 8A-8E illustrate the process of controlling design features. The residual limb with vulnerable locations highlighted in red (FIG. 8A), and most suitable loading sites highlighted in green (FIG. 8B). These can be compared to an FEA derived relative displaceability map visualized on the skin surface (FIG. 8C), which can be used to inform socket feature controlling design maps (FIG. 8D) and (FIG. 8E). White ellipses denote adjusted regions.

FIGS. 9A-9D illustrates four socket design strategies (1-4). The set of images on the left are visualizations of the spatial variation of the socket material parameter c (units MPa). The set of images on the right visualize the spatially varying fitting pressures at the skin surface (units kPa). Design 1 is a rigid socket with a constant fitting pressure. Design 2 is a rigid socket with a spatially varying fitting pressure. Design 3 features a compliant socket with spatially varying material properties and fitting pressures. Design 4 is similar to 3 except that its design map has been altered at the fibular head and the distal end of the tibia. The rigid material regions for designs 3 and 4 are highlighted in red and are rigidly supported.

Figure 10:
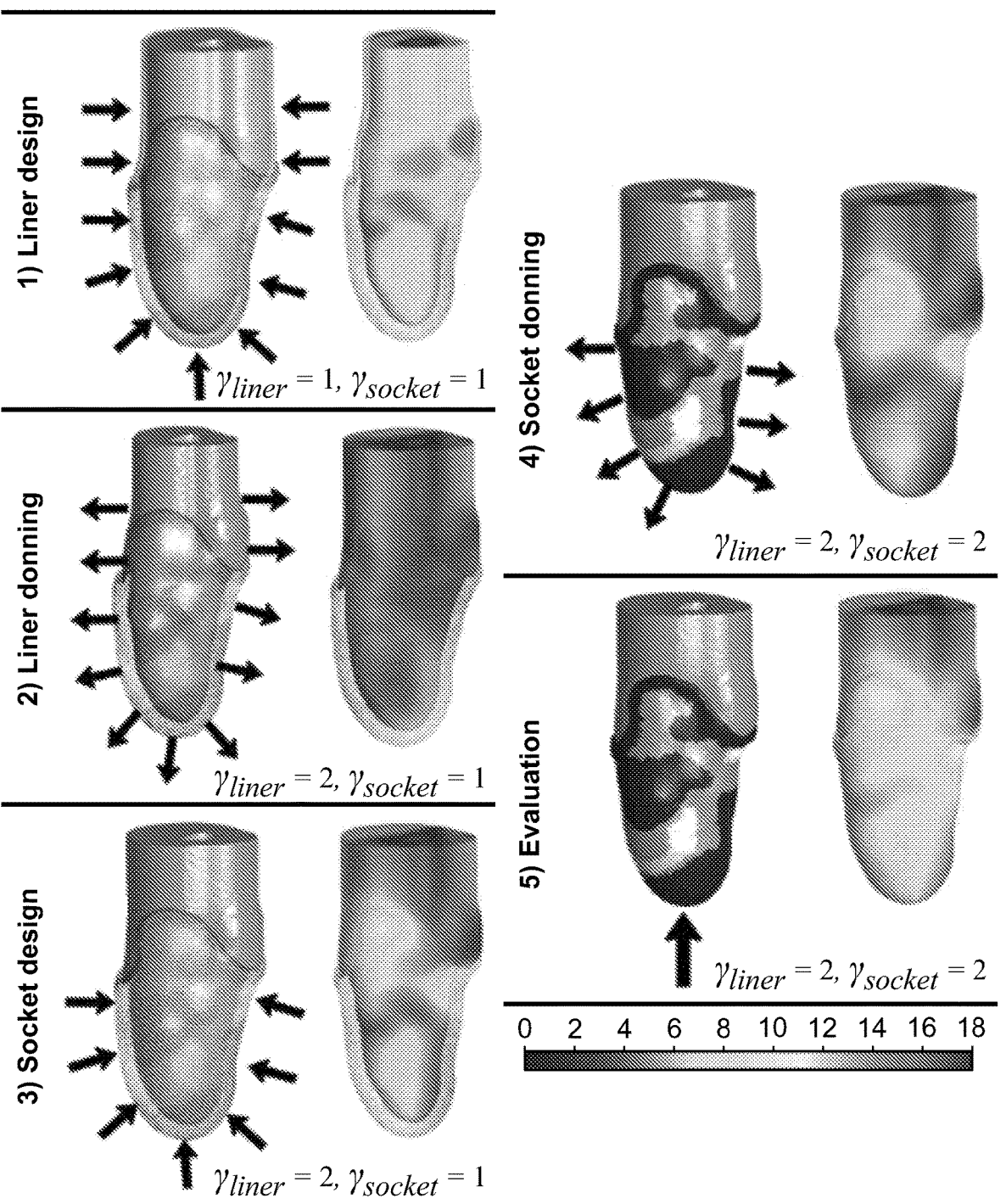

FIG. 10 shows a 5 step FEA liner and socket design and evaluation procedure. The column on the left shows schematic illustrations for the process in each step. The column on the right shows the model shaded towards total displacement (mm) to visualize the shape changes. Model regions are shown as opaque or transparent, respectively, to denote that they either do, or do not have significant mechanical properties assigned to them.

Figures 11A, 11B, 11C, 11D, 11E, 11F:
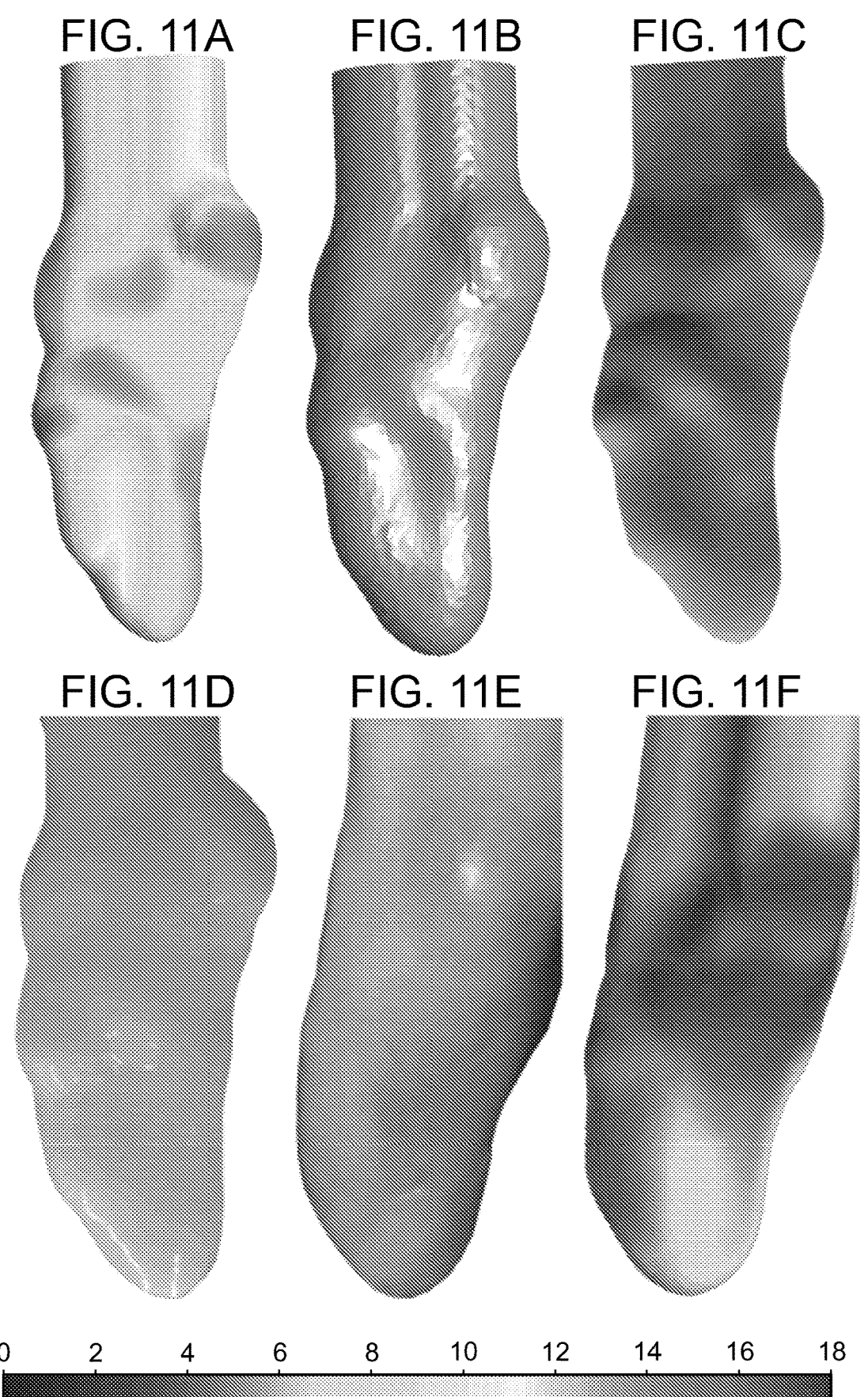

FIGS. 11A-11F Illustrate liner manufacturing. The inner surface of the FEA derived liner design (at the end of step 1 of the FEA process) (FIG. 11A) can be exported to a CAD file (FIG. 11B), which can be 3D printed to serve as a liner mold (FIG. 11C) for silicone liner production (FIG. 11D), after donning the liner on (FIG. 11E) its shape qualitatively resembles that of the liner at the end of step 2 in the FEA process (FIG. 11F).

Figures 12A, 12B, 12C, 12D, 12E:
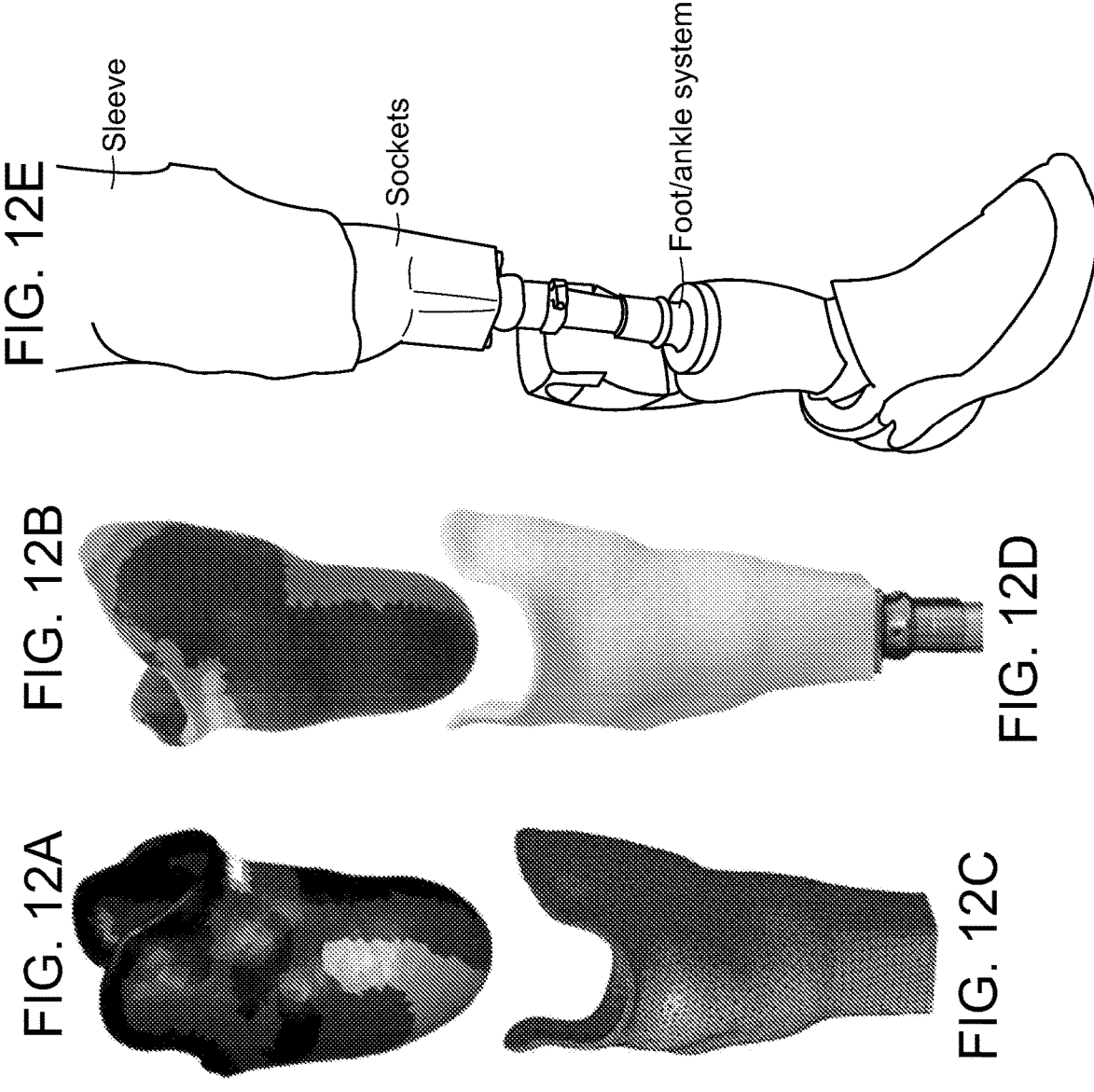
Figure 13A:
Figure 13A:
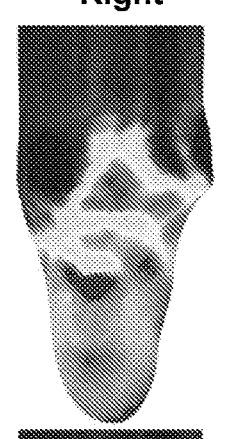
Figure 13A:
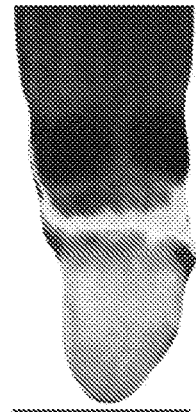
Figure 13B:
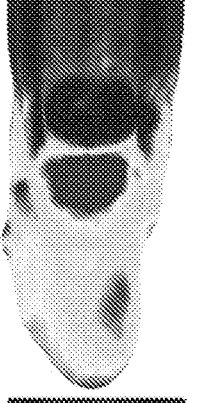
Figure 13B:
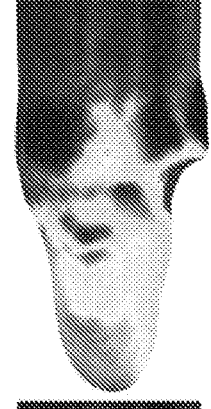
Figure 13B:
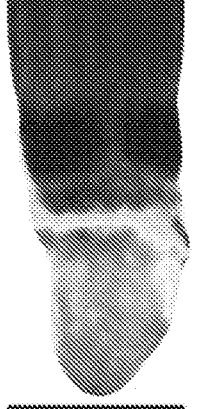
Figure 13C:
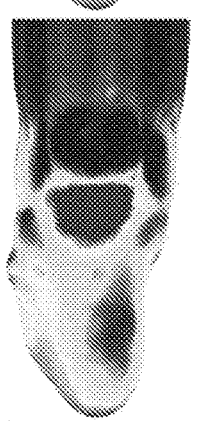
Figure 13C:
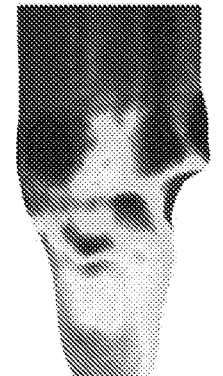
Figure 13C:
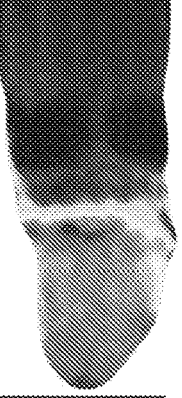
Figure 13D:
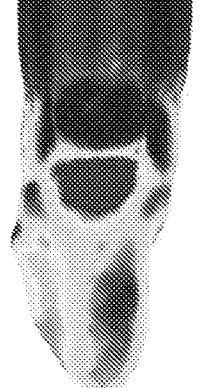
Figure 13D:
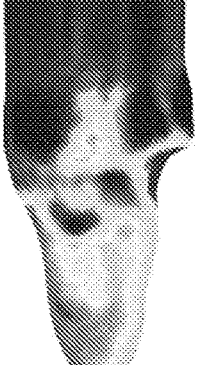
Figure 13D:
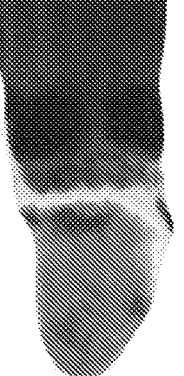
Figure 14A:
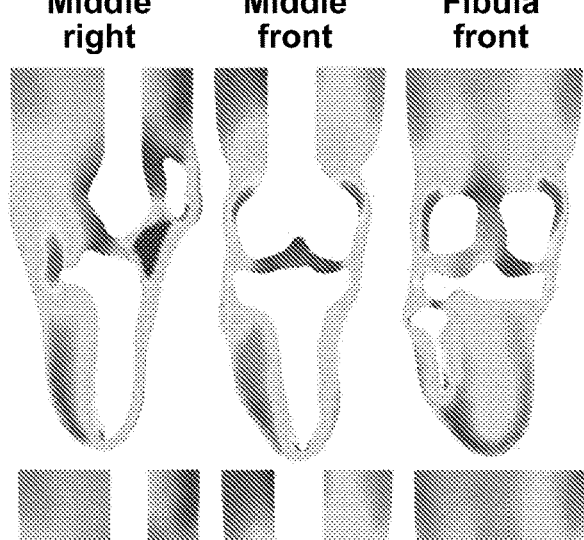
Figure 14B:
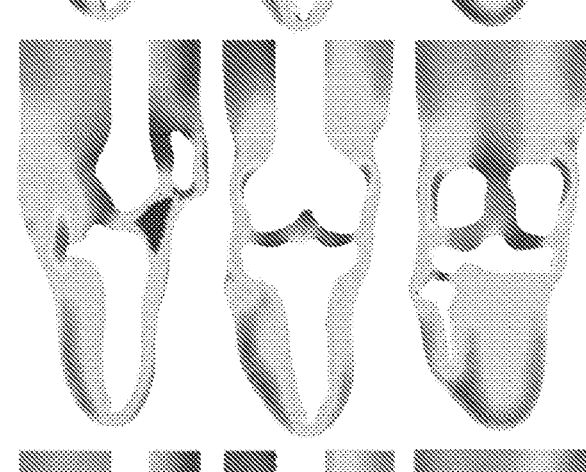
Figure 14C:
Figure 14D:
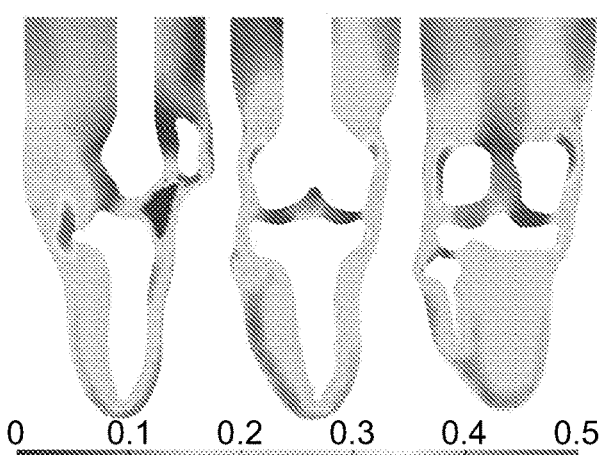

FIGS. 12A-12E illustrate socket manufacturing. A compliant socket design (FIG. 12A) can be 3D-printed in multiple materials (FIG. 12B), and can be used to automatically generate an outer socket design (FIG. 12C) printed in a rigid material (FIG. 12D); the compliant socket can be inserted into the outer socket, which can be connected to the foot/ankle system (FIG. 12E).

FIGS. 13A-13D show simulated skin surface pressure data for the 4 design variations. Units of pressure are kPa.

FIGS. 14A-14D show simulated internal tissue maximum shear strain (Green-Lagrange) data for the 4 design variations. Slice views are shown to highlight deformations at the tibia and fibula regions.

Figure 15:
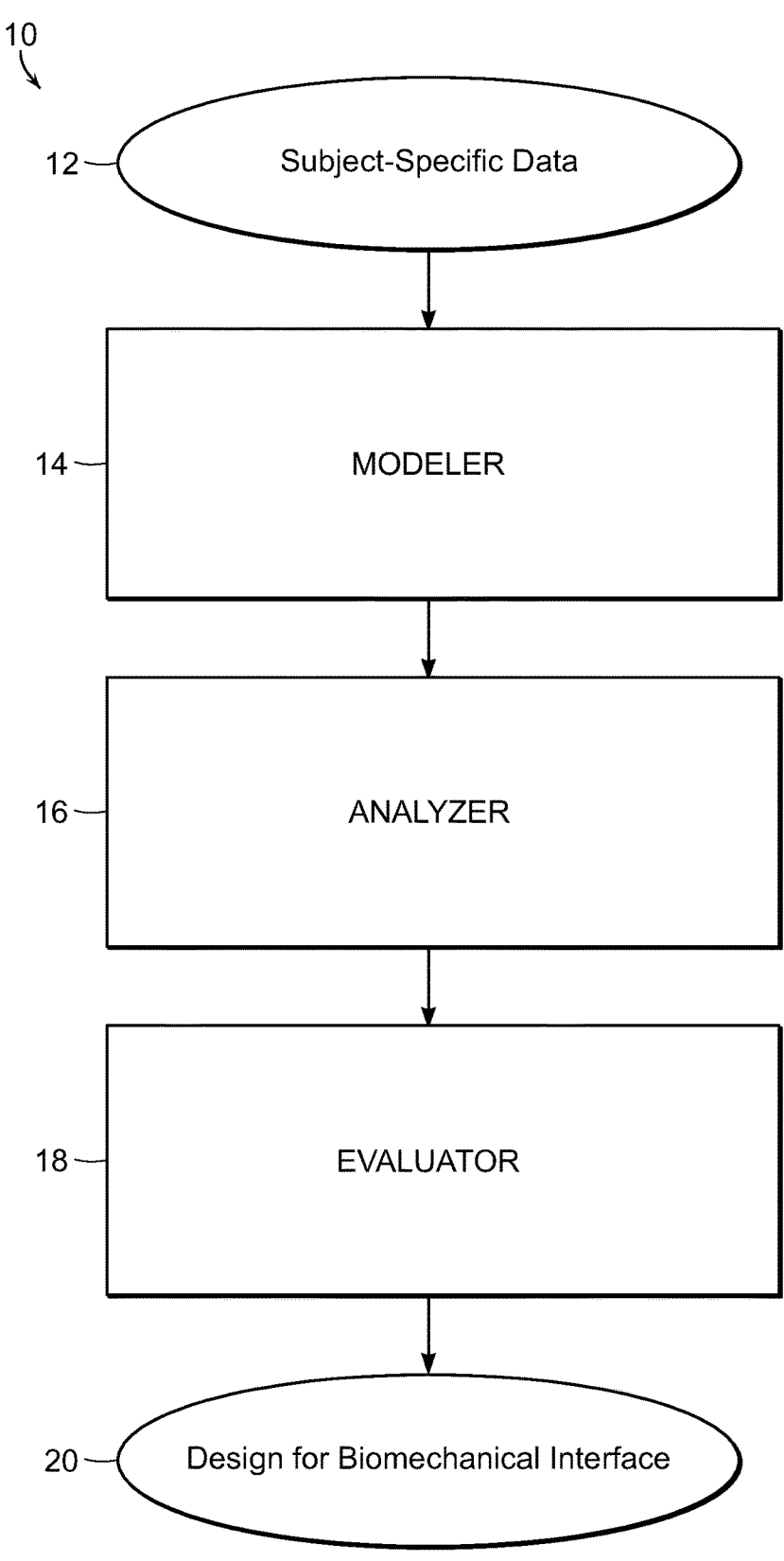

FIG. 15 shows an embodiment of the invention whereby the invention is a system for designing a biological body segment of a subject.

The foregoing will be apparent from the following more particular description of example embodiments of the invention, as illustrated in the accompanying drawings in which like reference characters refer to the same parts throughout the different views. The drawings are not necessarily to scale; emphasis instead being placed upon illustrating embodiments of the present invention.

SUMMARY OF THE INVENTION

The invention generally is directed to a method and system for designing a biomechanical interface of a device contacting a biological body segment of a subject.

In one embodiment, the method includes forming a quantitative model of the biological body segment from subject-specific data, the subject-specific data including geometry of the biological body segment. A biophysical analysis is conducted to thereby establish a relationship between the quantitative model and at least one feature of a biomechanical interface contacting the biological body segment, the at least one feature being associated with physiological benefit of the biological body segment. Physiological benefit may relate to maintaining or optimizing appropriate physiological conditions such as optimal health, tissue temperature, state of tissue loading, tissue circulation, tissue perfusion, or the comfort of the body segment. The relationship is applied to the at least one feature of the biomechanical interface contacting the biological body segment to thereby obtain an interface design for the biomechanical interface of the device.

The relationship between the quantitative model and the at least one feature of the biomechanical interface contacting the biological body segment allows local or global quantitative model outcomes to inform local or global features of the biomechanical interface. Quantitative model outcomes include deformations (e.g. stretch, strain) or loading (e.g. stress, pressure) on the tissue. Features of the biomechanical interface include thickness, porosity, stiffness, anisotropy and structure. Examples of relationship types include a functional relationship and a generative relationship.

In another embodiment, the invention is a system for designing a biomechanical interface of a device contacting a biological body segment of a subject. The system includes a modeler that generates a quantitative model of the biological body segment from subject-specific data, the subject-specific data including geometry of the biological body segment. An analyzer conducts a biophysical analysis, to thereby establish a relationship between the quantitative model and at least one feature of a biomechanical interface contacting the biological body segment, the at least one feature being associated with physiological benefit of the biological body segment. An evaluator applies the relationship to the at least one feature of the biomechanical interface contacting the biological body segment to thereby obtain a design for the biomechanical interface of the device.

The method and system of the invention provides a set of tools for subject-specific, data-driven, and automated design and evaluation of a prosthetic socket. This forms a significant advancement over current procedures which often are insufficiently data-driven, manual, not repeatable (dependent on prosthetist experience), and require repeated subject involvement for design evaluation. In contrast, the presented framework allows data-driven and automatic procedures and offers the ability to perform virtual iterative design evaluation thereby reducing subject involvement. Since the entire pipeline, from MM segmentation to FEA and CAD file export for 3D digital fabrication, is managed in a single automated framework, repeatability and geometric fidelity are guaranteed.

The method and system of the invention combine the use of significantly deformable socket designs and considers donning induced pre-loading due to both the liner and the socket components. The donning procedure presented herein utilizes multi-generational materials (see also: [47]). Using this approach, the subject-specific liner and socket source geometries can be morphed and generated using FEA such that the liner, socket and tissues are each in a pre-loaded and deformed state following the donning process. The donning process here follows from the application of pressure fields which are ramped down after the liner or socket layers have been defined fully, allowing the tissue to relax into the fitted liner and socket. This approach provides a computationally efficient means to simulate donning procedures.

The method and system of the invention offer data-driven and subject-specific liner and socket design, which benefits amputees because this approach offers a fully data-driven and subject-specific design (shape and impedance) and design optimization procedure. The applications are not limited to sockets for limb amputees. The method can easily be adjusted for FEA-based optimization of other biomechanical interfaces, such as for optimization of interfaces for wearable devices, for the design of optimal support structures, pressure ulcer prevention padding, bike seats, bras, and footwear.

The design process can be driven by subject-specific data and quantitative measurements, and design evaluation and optimization can incorporate subject-specific data and computational modeling based "virtual prototyping." There are several challenges to overcome to create such a framework:

1) non-invasive imaging to assess both external and internal tissue geometries, 2) consideration of realistic biomechanical material behavior, 3) design evaluation that employs detailed computational modeling to predict the subject-specific in-vivo tissue loading conditions (reducing the degree of subject involvement), 4) computational modeling that includes tissue pre-loading induced by both the liner and socket, and 5) production that employs CAM techniques to guarantee the fidelity of the design.

The method and system of the invention addresses these challenges with a quantitative, data-driven and subject-specific socket design process that incorporates: 1) imaging to accurately record tissue geometries, 2) indentation testing for tissue biomechanical behavior analysis, 3) FEA model development informed by the subject-specific imaging and indentation data, 4) FEA-based design and optimization to predict liner and socket equilibrium shape and impedances, and 5) the ability to export derived CAD files for the liner and socket for 3D printing-based manufacture of the compliant and spatially varying stiffness designs. The method and system of the invention, at least in one embodiment, enable formulation of specific socket interfaces and a plurality of strategies for designing a biomechanical interface of a device.

For example, in order to accurately evaluate the deformations and loading conditions of the soft tissue inside a socket, a finite element analysis (FEA) considers the following three loading effects: 1) Liner induced pre-loads (i.e. the loading effect of putting on an often tight liner), 2) socket induced pre-loads (i.e. the loading effect of donning or putting the fitted socket on), 3) loading occurring during functional use (e.g. standing/walking).

Embodiments of the invention ensure user physiological benefit, avoid soft tissue injury, and enhance the quality of life for the prosthetic user. The subject-specific, data-driven biomechanical interface method of the invention involves: 1) imaging to accurately record tissue geometries, 2) indentation testing for tissue biomechanical behavior analysis, 3) FEA model development informed by the subject-specific imaging and indentation data, and 4) FEA-based design and optimization to predict liner and socket equilibrium shape and impedances. Uniquely, the FEA predicts equilibrium shapes and compliant mechanical properties, and accurately simulates pre-load induced by donning, of both the liner and socket systems independently. FEA evaluation provides detailed information on internal and external tissue loading conditions that are, when excessive, directly responsible for soft tissue discomfort and injury. Hence, iterative design evaluation based on FEA may be used to optimize interface design, reducing the requirement for user involvement compared to conventional design approaches. The output of the framework can be directly used for computer-aided manufacturing (e.g. 3D printing). An embodiment of the invention, through comparison of several design strategies, confirms quantitatively what has to date only been approached qualitatively, namely that 1) alterations in the equilibrium shape of the socket can be used to locally enhance or reduce loading, and 2) compliant socket features can aid in relieving local surface pressure. Although a prosthetic socket interface is described herein, it will be understood by those of ordinary skill in the art that the automated computational framework for interface design described herein may be employed to design any other wearable device including, but not limited to, orthoses, exoskeletons, bras and shoes. Further it is clear the biomechanical interface(s) may not be part of a wearable device but part of a device or system interacting with a biological body segment; examples of such interfaces include the handles of tools, or the interface between a subject and support technology such as a seat or a subject's foot and a floor. In addition, it is clear that the biomechanical interface technology presented may apply to body segments of human and non-human organisms.

The presented biomechanical interface design framework employs non-invasive imaging and testing to determine local subject-specific geometry and biomechanical properties. These data are then used to fully drive the design process through the creation of a predictive and quantitative biophysical model which captures the non-linear elastic nature of tissues through the use of finite strain formulations. The subject-specific data and the biophysical model are subsequently used to automatically generate, evaluate, and iteratively optimize the design of a biomechanical interface. The design generation, evaluation and optimization, based on the biophysical modelling, forms a virtual prototyping methodology which captures not only donning induced pre-loading (the loading due to putting the device on) as well as subsequent additional loading due to functional use of the device. Further compliant interfaces can be designed which may undergo finite deformations during both the donning and loading phases.

DETAILED DESCRIPTION OF THE INVENTION

Despite advances in computer aided design technologies current design methodologies for biomechanical interfaces are not fully data-driven and are manual in nature, i.e. the design process may in some cases be computer aided, but has not been computer driven such that a computational system (rather than a human) performs the action of designing. Although some have used biophysical analysis (such as FEA) to evaluate loading of manually created designs, FEA (or a similar computational biophysical technique) has not been used for automated generation of designs, and has not been combined with automated iterative design evaluation and optimization. Further, current biophysical analyses have often considered soft tissue to be linear elastic and only relatively rigid socket materials have been employed. Finally, donning induced pre-loading of the biomechanical interface device and the soft tissue have not been incorporated in frameworks for design and design evaluation.

A need in the field of prosthetics is a design and manufacturing framework for biomechanical interfaces based on a clear scientific rationale to maximize comfort and avoid tissue injury. Such a computational design and manufacturing process would provide an accurate, repeatable and fully subject-specific data-driven process, and can also be combined with virtual prototyping techniques for subject-specific design optimization. Virtual prototyping can be realized through finite element analysis (FEA), allowing for the detailed investigation of tissue pressures and internal deformations. FEA based optimization may potentially reduce the need for repeated test socket manufacturing and iterative subject involvement, and is therefore also able to reduce the overall cost and manufacturing time required.

In order to accurately evaluate the deformations and loading conditions of the soft tissue inside a socket, the FEA should consider the following three loading effects: 1) Liner donning induced pre-loads, 2) socket donning induced pre-loads, and finally 3) loading occurring during functional use (e.g. standing/walking).

The accurate simulation (using large strain formulations and non-linear FEA) of pre-loading has to date not been combined with the evaluation of significantly deformable and compliant socket designs. In addition, pre-loading of the soft tissue due to both a liner and a socket have to date not been investigated.

In the above-discussed approaches, the socket design process is based on human experience, and design evaluation and optimization is manual, involving iterative refinement with repeated subject involvement. Ideally however, the design process should be driven by subject-specific data and quantitative measurements, and design evaluation and optimization should incorporate subject-specific data and computational modeling based "virtual prototyping." There are several challenges to overcome to create such a framework: 1) non-invasive imaging is required to assess both external and internal tissue geometries, 2) realistic biomechanical material behavior needs to be considered, 3) design evaluation should employ detailed computational modeling to predict the subject-specific in-vivo tissue loading conditions (reducing the degree of subject involvement), 4) computational modeling should also include tissue pre-loading induced by both the liner and socket, and 5) production should employ CAM techniques to guarantee the fidelity of the design.

To address the discrepancies of current biomechanical interface design and manufacturing processes, and explore the use of compliant materials, a novel quantitative, data-driven and subject-specific biomechanical interface design framework is presented here. The framework incorporates: 1) MRI for the generation of accurate subject-specific computation model geometries, 2) the use of non-invasive tissue mechanical property assessment based on indentation tests, 3) automated anatomical landmark and biomechanical behavior driven design, 4) spatially varying design features such as donning induced pre-load, and material stiffness, 5) evaluation of interface induced pre-loading, 6) finite element analysis based subject-specific design evaluation, 7) the 3D printing based manufacture. Using the novel framework 4 design strategies are compared in terms of predicted contact pressures and internal strains.

The invention generally is directed to a method and system for quantitatively designing, and computationally evaluating, subject-specific mechanical interfaces that connect a device to a biological body segment.

The method of the invention generally is a method for designing a biomechanical interface of a device contacting a biological body segment of a subject. The method includes forming a quantitative model of the biological body segment from subject-specific data, the subject-specific data including geometry of the biological body segment. A biophysical analysis is conducted to thereby establish a relationship between the quantitative modeling and at least one feature of a biomechanical interface contacting a biological body segment, the at least one feature being associated with physiological benefit of the biological body segment. A "biophysical analysis," as that term is understood herein, is a numerical analysis process involving the simulation of biophysical phenomena (this includes continuum mechanical analysis of biomechanical processes such as tissue deformation, swelling, and/or heating in response to loading). The biophysical analysis relies on numerical techniques to solve systems of partial differential equations; examples of such numerical techniques include finite element analysis (FEA), finite difference methods, finite volume methods, isogeometric analysis, boundary element methods, and meshfree methods. The relationship is applied to the at least one feature of the biomechanical interface contacting the biological body segment to thereby obtain a design for the biomechanical interface of the device.

The relationship between the quantitative model and the at least one feature of the biomechanical interface contacting the biological body segment can be a functional relationship or a regenerative relationship.

A "functional relationship," as that term is understood herein, defines a mapping, such as a mathematical mapping, whereby local or global quantitative model outcomes can be used to inform local or global features of the biomechanical interface. An example of such a functional relationship is to map quantitative model predicted spatially varying displacement data (e.g. in response to an applied pressure) to the spatially varying material stiffness of the biomechanical interface.

A "generative relationship," as that term is understood herein, is one which may deviate from a direct mathematical mapping and is instead part of an iterative procedure or one relying on a multitude of model outcomes. In the iterative approach quantitative model findings of the current iteration inform changes to features of the biomechanical for the next iteration. At each step in the iterative process features of the biomechanical interface are adjusted in response to quantitative model outcomes. The generative relationship in this case defines the rule for adjustment of the features based on the quantitative model outcomes. Iterative alteration of the features of the biomechanical interface may be part of a systematic or stochastic optimization process, or a generative process. Formulating the relationship may depend on the outcomes of a multitude of quantitative analyses or a multitude of quantitative model outcomes for an array of design variations. Such a library, bank or array of quantitative model data may then be combined with (e.g. neural network based) machine learning to propose improvements to local or global features of the biomechanical interface. In this case the generative relationship is formed by the analysis of the machine learning system on the training data set formed by the bank of quantitative model outcomes.

The method can further include the step of optimizing the at least one feature for physiological benefit of the biological body segment in the biomechanical interface based on the biophysical analysis. An example is optimization based on iterative biophysical analysis whereby an objective function is minimized using optimization methods (such as gradient descent methods or genetic and evolutionary algorithms). The method can further include the step of fabricating a support of the biomechanical device having the optimized feature.

Composing the quantitative model can include at least one non-invasive imaging method selected from the group consisting of magnetic resonance, x-ray, ultrasound, optical methods and optical tomography, thermography and elastography, to form a non-invasive image. In one specific version of this embodiment, the method includes the step of imaging tissue adjacent to the biological body segment. Also, forming a quantitative model can further include employing the non-invasive imaging method to form an external tissue geometry and an internal tissue geometry of the biological body segment. The geometry data includes at least one of the following: points, curves, and surface descriptions. The geometric descriptions can be either mesh based on non-mesh based and can be either parameterized or non-parameterized. An example of parameterized geometry is surface geometry based on non-uniform rational basis splines (NURBS), and an example of non-parameterized geometry is surface geometry derived using level set methods. In one embodiment, forming the quantitative model can include inferring geometry of the biological body segment through dedicated biophysical modeling and/or statistical shape modeling. In another version of this embodiment, the external tissue geometry and the internal tissue geometry are formed (e.g. through the use of level set methods) by segmenting the non-invasive image data. Once a geometric description of the biological body segment is created it can be used to automatically generate the source geometry (a geometry which is derived by locally copying the shape of the biological body segment) for the biomechanical interface. This source geometry can be directly used to fabricate a biomechanical interface design or the source geometry can be morphed (i.e. changed shape) and optimized through biophysical analysis.

The biophysical modelling may include input from measurements of biomechanical material properties. Biomechanical material property assessment is here based on either a contact method or non-contact method. A contact method is one relying on the application of an external transducer or actuator to mechanically perturb the tissue, e.g. through vibration or indentation, combined with measurement and analysis of the tissue response. An example of the former is magnetic resonance elastography, and another example is indentation combined with at least one of the following measurements, indentor force, indentor displacement, and tissue deformation. A non-contact method is one whereby the biomechanical property measurements do not rely on the application of a mechanical perturbation with a device touching the body; instead, the properties can be derived from analysis of external and non-invasive measurements. Examples of the latter are water tank based ultrasound and ultrasound elastography methods. For both the contacting and non-contacting methods the biomechanical properties may be derived directly from post-processing of the measurements or may be determined from dedicated biophysical analysis. An example of the use of post-processing is biomechanical property derivation from slope analysis of force-displacement data. An example of the use of biophysical modeling, and a particular embodiment of the biomechanical property analysis, is the use of indentation experiments, whereby indentation force and displacement is measured, which is then combined with inverse FEA based determination of the biomechanical properties. The biomechanical material property analysis can include analysis of at least one biomechanical property selected from the group consisting of, for example, impedance, damping, stiffness, the shear and bulk modulus (or any other stiffness or compliance tensor component), and other elastic, hyperelastic, viscoelastic, and poroelastic properties or constitutive parameters of the tissues. The biomechanical property assessment can be used to locally inform the biomechanical behavior in the biophysical analysis. By incorporating the biomechanical properties in the biophysical analysis, and through the use of appropriate constitutive modeling, the biophysical analysis can be used to simulate the physical interaction of the biological body segment with a biomechanical interface device. Such biophysical analysis allows for evaluation of biophysical measures relating to physiological benefit, which may include at least one of the following: tissue loading, tissue surface pressure, tissue strain, tissue stress, tissue temperature, tissue swelling, and tissue porosity.

In another embodiment, the method further includes the step of pre-processing the source geometry such as by surface fairing and smoothing, and remeshing, and the regularization and smoothening of parameterized (e.g. NURBS) descriptions. Preferably, the pre-processing includes surface fairing and smoothing, such as by Laplacian surface smoothing. In addition to surface fairing and smoothing, pre-processing can include remeshing, such as by refinement and iterative mesh optimization.

Wherein the quantitative model of the biological body segment is employed to form a source geometry, the method can further include the step of conducting the computer-aided design process on the source geometry that includes at least one member of the group consisting of cutting, merging, extruding, thickening, offsetting, lofting, bending and sweeping.

In yet another embodiment of the method that includes forming a source geometry, wherein the biological body segment is in an unloaded state, the method can further include the step of mapping the interface design to the biological body segment, wherein the biophysical analysis is employed to adjust the source geometry to thereby obtain a fit of the source geometry to the biological body segment. In one version of this embodiment, the fit includes forming a biomechanical competition model that is formed by a method, such as by forming a design map of constraints that relate loading of the biological body segment to loading on interface design. In one specific version of this embodiment, the loading type is at least one member of the group consisting of a force, pressure, stress, traction. In a still more specific version of this embodiment, the design that includes at least one response of the biological body segment selected from the group consisting of deformation, displacement, stress, strain, stretch, and pressure. In one specific embodiment, the design map is a displaceability map, such as, for example, where the design map is correlated to at least one design feature of the biomechanical interface selected from the group consisting of a design driving pressure, a local thickness of the tissue, a local material impedance of the tissue. In one such version of this embodiment, the design feature is the design driving pressure, wherein the design driving pressure can include at least one member selected from the group consisting of a homogeneous pressure, a spatially-varying pressure linearly related to a displaceability map, and a spatially-varying pressure relating to the displaceability map and including a plurality of functions corresponding to distinct anatomical regions. In one version of this embodiment, the design driving pressure is spatially-varying but with separate mappings for specific anatomical regions (e.g. for a prosthetic socket the patellar ligament region, the fibular head region, and the remainder of the body segment may be represented by separate mappings). In another version, the functions include a linear function. In another embodiment, the functions include a non-linear function, such as wherein the non-linear function includes at least one member selected from the group consisting of an exponential function, a hyperbolic function and a polynomial function.

In one embodiment of the invention, wherein forming a biomechanical computational model includes forming a design map of constraints that relate loading of the biological body segment to loading on the interface design, the at least one feature of the biological interface contacting the body segment that is associated with physiological benefit of the body segment is at least one member of the group consisting of interface-skin pressure, tissue strain, tissue stress, tissue pressure, tissue temperature, tissue swelling.

In an alternate embodiment of the method, wherein forming the biomechanical computational model includes forming a design map of constraints that relate loading on the biological body segment to loading on the interface design, establishing a relationship (e.g., a functional relationship) between the quantitative model and the at least one feature of the biomechanical interface contacting the biological body segment further includes the steps of: donning the biomechanical interface in place by preloading the biological body segment at the biomechanical interface, wherein the biomechanical interface is in an unloaded state; relaxing the constraints, whereby the biological body segment mechanically interacts with the biomechanical interface, thereby loading the biomechanical interface and causing the biological body segment and the biomechanical interface device to be in a pre-stressed state; and correlating the pre-stressed state to the feature of the biomechanical interface to be improved for physiological benefit of the biological body segment, thereby relating (e.g., functionally relating) the quantitative model of the biological body segment and the feature of the biomechanical interface. In one version of this embodiment, the biomechanical interface is in a deformed state after relaxation of the constraints. In another version, the step of applying the relationship between the quantitative model and the at least one feature includes a second biophysical analysis distinct from the biophysical analysis that establishes the relationship between the quantitative model of the biological body segment and the at least one feature of the biomechanical interface. In one version of this embodiment, the second biophysical analysis includes an interactive optimization scheme. In one specific version of this embodiment, the iterative optimization scheme includes an optimization algorithm that is at least one member of the group consisting of a genetic, evolutionary and gradient descent method. The iterative optimization scheme can include, for example, evolution equations of at least one of shape, material properties (e.g. biomechanical parameters, anisotropy, viscoelasticity) and lattice structures.

In certain embodiments, donning the biomechanical interface can include employing a member selected from the group consisting of a rigid socket having a homogeneous fitting pressure, a rigid socket having a spatially varying fitting pressure, and a compliant socket having a spatially varying fitting pressure and especially varying socket stiffness. In a specific embodiment, donning the biomechanical interface can include employing a compliant socket having a spatially varying fitting pressure and a socket material stiffness over a distal end and over fibular head of the biological body segment.

Another embodiment of the invention is a system for designing a biomechanical interface of a device contacting a biological body segment of the subject. In one embodiment, the system comprises: a modeler configured to generate a quantitative model of the biological body segment from subject-specific data, the subject-specific data including geometry of the biological body segment; an analyzer configured to conduct a biophysical analysis to thereby establish a functional relationship between the quantitative model and at least one feature of a biomechanical interface contacting the biological body segment, the at least one feature being associated with physiological benefit of the biological by segment; and an evaluator configured to apply the functional relationship to the at least one feature of the biomechanical interface contacting the biological body segment to thereby obtain a design for the biomechanical interface of the device.

The invention, in at least one embodiment, is an automated and data-driven computational framework for the design and optimization of biomechanical interfaces. The framework, described herein as directed to the optimization of the biomechanical interface of prostheses for transtibial amputees, can also be applied to the optimization of biomechanical interfaces in general (e.g. the optimization of shape and mechanical properties of shoes, the frame for eyeglasses, the support structures on wheelchairs, and orthopedic supports). In the case of transtibial prosthetic devices, the biomechanical interface can be formed, in one embodiment, by both a prosthetic liner and a socket. The invention, at least in one embodiment, enables data-driven and subject-specific optimization of both features.

In one embodiment, the method of the invention includes, generally, the steps of: 1) subject-specific data acquisition; 2) computer-driven design and computational modeling; 3) design evaluation and optimization; and 4) manufacturing. During the first step, subject-specific data are recorded. An important outcome of this step is a description of the subject-specific tissue geometries e.g. based on imaging techniques. Non-invasive imaging techniques can be used such as x-ray, optical, ultrasound and MM. These imaging strategies provide both the external and internal tissue geometries. However, optical measurements can also be employed, but only for external skin surface geometry. Combined with a library of 3D models with known internal geometries (e.g. established from in-vivo medical imaging techniques) such external measurements can be combined with techniques like statistical shape modeling to infer the internal geometries instead. In the example for prosthetic interface design, MM is employed. Besides geometry, subject-specific biomechanical material property analysis is also required. This can be based on indentation testing (e.g. combined with inverse finite element analysis) or elastography methods (e.g. magnetic resonance elastography and ultrasound elastography).

In this embodiment, the second step of the method involves data-driven, automated design through the use of computational modeling. The design features of the biomechanical interface can be specified manually, or, as proposed herein, through a fully data-driven methodology in an automated fashion. The unloaded tissue geometries of the biological segment of interest can be used to define the source geometry for the design of the biomechanical interface. The term "source geometry," as defined herein, refers to unloaded subject geometry from which an interface design is either fully or partially derived. This source geometry can be morphed into an altered shape, e.g. to provide a design with an enhanced fit. In other words, the design of the biomechanical interface starts off as being derived directly from the tissue geometries of the biological segment of interest (termed "source geometry") but can be morphed or molded or adjusted into a final interface design. The image data, and the resulting tissue geometries, may extend further than the biological segment intended for the biomechanical interface. In a specific embodiment, these surrounding tissue regions may be required for accurate computational modeling of the interaction of the biomechanical interface with the tissue or biological segment. Descriptions of the boundaries, and other design features, of the biomechanical interface may be linked to subject-specific features such as anatomical landmarks. The boundary definition and landmarks are thus identifiable from the image data or the derived subject geometries, in an automated way. The source geometry can also be pre-processed in and automated fashion e.g. using surface fairing and smoothening (e.g. Laplacian surface smoothening), re-meshing (e.g. refinement and iterative mesh optimization), and other geometry enhancement techniques. In addition, computer aided design processes can be performed on the source geometry, such as cutting, merging, extrusion, thickening, offsetting, lofting, blending, and sweeping. Such operations can be programmed to occur automatically on the derived geometric models. Once the desired source geometry is obtained it is ready for morphing. By morphing the source geometry, a particular desired fit is obtained. Aspects like tightness of the fit depend both on the amount of adjustment of the shape but also on the human user tissue geometries and mechanical properties. For instance, a local tissue compression can result in high stresses, high surface pressures, and a tight fit for a region that is stiff and/or thin with respect to the level of compression. However, for the same level of compression the pressures may be low and the fit loose if the tissue region is relatively soft and/or thick. In order to determine the appropriate fit characteristics, accurate knowledge of the tissue biomechanical behavior is required. This includes the geometry and the mechanical properties of the tissue region. In the current framework the morphing will be based on subject-specific biomechanical data and computational modeling.

A biomechanical computational model of the tissue region is constructed. In one embodiment, the goal of the dedicated computational model is to evaluate the tissue region's response (e.g. in terms of deformation, displacement, stress, strain, stretch, and pressures) to an applied loading (e.g. pressure, stresses, tractions, and forces) relevant to the design. A measure of the tissue response to the loading can inform a map to define design features (such as the spatial variation of the amount of pre-loading, the local thickness, and the local material stiffness) of the biomechanical interface. The mechanical properties for the tissue region of the computational model are informed by, for example, dedicated mechanical indenter tests or elastography imaging methods. The computational model is then subjected to a desired loading regime to evaluate the local tissue response to that loading. This is conceptually similar to the prosthetist palpating the tissue to estimate the biomechanical behavior qualitatively. For instance, the response to pressure loading can be used to define a map of displaceability due to the known applied load. For the example presented here in the context of liner and socket design, the loading is formulated by pressure fields. Regions with high displaceability demonstrate larger displacements due to the applied pressure in the computational model than regions of low displaceability. Hence, the computational modeling of the subject-specific biomechanics may provide a map of displaceability. Although a constant pressure field is used herein to provide local skin surface total displacement (displaceability), other loading regimes can be envisaged such as constant or spatially varying pressures, tractions, normal or shear forces. In addition, other map types can be evaluated, i.e. instead of a map of displaceability other mechanical outcomes can be used such as tissue deformation tensors, strains, stretches, pressures and stresses. The map is referred to as a "design map" since it may be used to inform design features of the biomechanical interface. Computational modeling-based design specification based on the design map offers a means to incorporate subject-specific, date-driven design features in an automated way. Once the map is defined it can be used to define local features such as interface shape, thickness, and material properties. In addition, the amount of pre-compression or pre-loading can be defined by such a map.

The design of biomechanical interfaces includes not only the complexity of the geometries and biomechanical behavior but also the fact that there is a mechanical interaction (load transfer and mutual deformation) between the interface device and the tissue region. After donning the biomechanical interface, both the interface and the tissue region are in a loaded and deformed state. Prediction of the final mechanical state of both the interface and the tissue region is resolved through computational modeling, using biophysical analysis, such as finite element analysis (FEA). FEA, for example, can be used to morph (i.e. change the shape of) the source geometry into a desired design based on a design map that relates tissue displaceability with interface equilibrium shapes and impedances. However, during the morphing process the interface design is in contact with the tissue region, developing stresses and strains during the morphing process. Once morphing is complete and the desired design (equilibrium shape) of the biomechanical interface is obtained, the material properties and mechanical behavior of the biomechanical interface are initiated. At this state the tissue region is pre-loaded and potentially deformed while the biomechanical interface is unloaded without stress. In a subsequent analysis step the constraints driving the morphing process (e.g. a pressure, force or stress system) are removed. As such, the tissue region will mechanically interact with the biomechanical interface and subject it to loading. Following this relaxation phase both the tissue region and the biomechanical interface device are in a pre-stressed and potentially deformed state. The process of morphing, assignment of mechanical properties and relaxation can be repeated for multi-layered structures as well such that different components or layers of the biomechanical interface have altered equilibrium shapes and altered pre-stresses following "donning," which is defined herein as the application and settling of the biomechanical interface. Once the biomechanical interface is donned in place and pre-loading is appropriately considered, the system can be evaluated for loading expected during functional use of the interface. This evaluation phase can occur based on FEA as well. Since the biomechanical interface design is automatically generated from the subject-specific data and FEA-based biomechanical evaluation, its functional performance can be optimized through an iterative optimization scheme. Such an optimization scheme or schemes can be based on optimization algorithms, e.g., genetic or evolutionary algorithms or gradient descent methods. Alternatively, design optimization can be achieved through evolution equations of shape and structure defining design adjustments for the next generation based on current and past evaluations.

The following are examples of various embodiments of the invention. They are not intended to be limiting in any way.

Materials and Methods

The following is a description of one embodiment of the method and system of the invention. The invention is not limited by the description that follows.

This section will outline: 1) an overview of the liner and socket design process, 2) non-invasive imaging, 3) obtaining subject-specific geometries, 4) creating the liner and socket source geometries, 5) solid meshing, 6) constitutive modeling, 7) controlling design features, 8) FEA based design and evaluation.

All data processing and visualization was performed using custom codes written in MATLAB® (R2015b The Mathworks Inc., Natick, MA) and using the open-source MATLAB toolbox GIBBON (r89, [48], [49], http://www.gibboncode.org/). All FEA was performed using the open source finite element software FEBio [50] (V2.3.1, Musculoskeletal Research Laboratories, The University of Utah, USA, http://febio.org/).

One skilled in the art will have general knowledge of non-linear continuum mechanics and tensor algebra. A more detailed description of non-linear continuum mechanics is provided in references [51]-[53] listed below, the relevant teachings of which are incorporated herein by reference in their entirety.

Overview of the Liner and Socket Design Process

FIGS. 3A-3K provide an overview of a possible embodiment of a fully data-driven prosthetic socket design process. Based on non-invasive image data (example shows MM) and segmentation of tissue contours (FIG. 3A), subject-specific surface geometry can be reconstructed (FIG. 3B). These can be used for FEA and indentation based subject-specific tissue mechanical property evaluation (FIG. 3C, see also [54]). Further, from the Mill derived geometry, anatomical landmarks can be identified (FIG. 3D) allowing for the automated creation of socket source geometries and combined FEA models (FIG. 3E). The socket source geometry is directly derived from the subject's unloaded geometry and therefore does not pre-load the tissue. Hence to formulate the final socket design its geometry needs to be altered to enhance loading at safe sites and prevent loading at vulnerable sites. Further compliant socket materials can be used to relieve loading. The design process developed utilizes spatially varying socket fitting pressures (FIG. 3F) which morph the socket into its desired fitted shape (shown schematically in FIG. 3G by the arrows acting on the tissue). Further, spatially varying mechanical properties can be assigned. By using multi-generational material theory [55] we are able to freely morph the socket design (without developing socket material stresses, hence the socket is shown as transparent in FIG. 3G) while donning induced pre-loads develop in the soft tissue. Once the desired socket equilibrium design is obtained the socket materials are defined, or "solidified" in a stress free state while critically the soft tissues have developed stresses due to this simulated fitting or donning of the socket. Using this process, the designs are therefore initiated, fitted and donned onto the subject (FIG. 3H). Next the designs are evaluated using FEA by applying body weight loading (illustrated schematically by an upward arrow in FIG. 3H) allowing for evaluation of skin surface pressures and soft tissue strains (FIG. 3I). Based on the simulated tissue loading conditions, the spatially varying socket materials and the fitting pressures can be iteratively optimized as indicated by the circularity of the process in FIG. 3F-3I. Once the iterative virtual test socket optimization process has converged on an optimal design, the socket design can be exported for 3D printing based manufacture (FIG. 3J see also [21]), creating a fully data-driven process to obtain the final socket FIG. 3K.

The FEA process starts with the unloaded subject geometry and socket and liner source geometries. These source geometries are not yet referred as designs, similar to a prosthetist's subject cast, these source geometries are simply copies of the unloaded subject geometry and are created by offsetting from the subject skin surface. The source geometries therefore need to be adjusted to create the desired socket and liner designs. An automatic and data-driven adjustment process is proposed here using FEA based morphing and fitting on the virtual subject. During FEA, geometries are simultaneously morphed into designs and donned onto the subject. Morphing of the source geometries takes place using so called fitting pressures. These are pressure fields applied to the skin surface which deform the subject geometry, while the source geometries still lack any mechanical strength and are freely carried along with the skin motion (without developing stresses). Once a desired equilibrium design shape is obtained the geometries are "solidified" during FEA by assigning them with appropriate and stress free mechanical properties. Next the fitting pressures are ramped down in FEA allowing the soft tissues to push back and relax into the devices. For compliant designs the tissue is now able to settle into and deform the devices until both are at (a donning induced pre-loaded) equilibrium. Using this process, the designs are therefore initiated, fitted and donned onto the subject. Next the designs are evaluated using FEA by applying body weight loading.

A liner is manufactured by 3D printing a mold which can be used to create a subject specific liner, for instance using silicone rubber liner (Dragon Skin® 10 FAST, Smooth-On, Inc., Macungie, PA, USA). The sockets can be manufactured using 3D printing. For rigid sockets the designs can be printed as a single part, and from a single material. For compliant sockets a spatially varying socket wall material is used. Such designs can be realized using a multi-material printer (Connex 500, Stratasys Ltd., Eden Prairie, Minnesota, USA). For the compliant designs the socket system consists of an inner and an outer socket. The inner socket is compliant while the outer socket is rigid and provides additional strength. The outer socket can be bonded to the inner socket at sites where the inner socket is stiff while it can be offset from the inner socket at compliant sites to allow for socket deformation.

Non-Invasive Imaging

In order to capture the anatomical structure and tissue geometries of the residual limb, Magnetic Resonance Imaging (MRI) is used. A male volunteer (age 48, weight 77 kg, activity level K3 [see also [2] on activity levels]) was recruited and placed prone and feet-first inside an Mill scanner (Siemens Magnetom 3 Tesla, Siemens Medical Systems, Erlangen, Germany). Informed consent was obtained and the research protocol was approved by the Committee on the Use of Humans as Experimental Subjects at Massachusetts Institute of Technology. All imaging was performed with a RF body coil and an Ultra-short $T_E$ Mill (UTE-MRI) sequence (e.g. [56]) was used, ($T_R/T_E$=5.71/ 0.07, acquisition matrix 192×192, 192 slices, field of view 220×220×220 mm, voxel size 1.145×1.145×1.145 mm) enabling visualization of bone tissue contours despite its short $T_2$ time. Several slices of the MRI data are visualized in FIG. 4A and FIG. 4B.

Obtaining Subject-Specific Geometries

In order to construct the detailed computational model, skin and bone contours were segmented (based on GIBBON [48] uiContourSegment function). Segmentation is applied to the raw image data and is based on adjustment, selection and combination of smooth iso-contour lines. After contours for a specific feature are recorded (FIGS. 4A and 4B) for each slice, these can be converted to a level set image which consists of the signed distance (internal is negative, external positive) of each image voxel center to the nearest contour point. Next level (or iso-) surfaces (FIGS. 4C-4D) can be constructed at the level 0 as this corresponds to the contours. The surface mesh quality is then improved by resampling the surface geodesically (homogenous point distribution) at a desired density, and by smoothing the surface based on shrinkage avoiding smoothing [57]. Following segmentation, the geometries are reoriented in two steps. First a rotation is performed such that the femur and tibia are aligned in the feet-head direction (z-axis). This direction is identified using principal component analysis of the bone surfaces coordinates. Next the model is rotated around the z-axis such that such that the front-back direction corresponds to the positive y-axis direction. This is achieved by rotating the geometry such that the XY-projection of the vector spanned between the center of the patella and the center of the femur, is most aligned with the y-axis. FIG. 4B shows how the image data and therefore the derived surface geometry does not extend far beyond the top of the patella. Since it was of interest to model beyond this region the surface geometry of the femur and skin was extended by 60 mm in the z-direction providing the extended geometry seen in FIG. 4D and elsewhere.

Creating the Liner and Socket Source Geometries

Similar to how the plaster cast in the traditional approach is used as source geometry to initiate the design process, the MRI derived subject geometry is used here. The source geometry for the liner is created by offsetting a layer from the skin surface. For the current study the liner thickness varied linearly from 4 mm to 6 mm from the top of the model to the distal end. Once the liner source geometry is defined the source geometry of the socket is formed by offsetting from the outer surface of the liner source geometry. However, first the socket upper boundary, known as the cut-line, is defined. The cut-line geometry is automatically constructed based on the anatomical landmarks shown as colored dots in (FIG. 5A): a=Patella bottom, b=Patella mean, c=Patella top, d=Patellar ligament middle, e=Femur middle front, f=Femoral condyle back right, g=Femoral condyle back left, h=Tibia middle top, i=Tibia left condyle top, j=Tibia right condyle top. Using ray tracing from these landmarks, outward to the skin surface, these landmarks can be used to define a set of curve control points {$p_{(1)}$, $P_{(2)}, \ldots, P_{(14)}$}, through which a smooth curve can be fitted (FIG. 5B). The source geometry for the socket is then formed by offsetting the region found under the curve by a desired thickness from the skin surface. A uniform socket wall thickness of 6 mm is used here and the socket cut-line rim was rounded with a rounding diameter matching the socket wall thickness. This creates the socket geometry shown in FIG. 5C.

Solid Meshing

For FEA the following four material regions are modeled: 1) the bulk soft tissue (which includes skin, adipose and muscle tissue), 2) the patellar ligament, 3) the liner, and 4) the socket. Bones were not modeled as solid materials but were instead represented by rigidly supported voids. The solid material regions were meshed using a total of 146502 tri-linear tetrahedral elements (see FIGS. 6A-6C) using the free and open source meshing code TetGen (version 1.5.0, www.tetgen.org, see [58]) integrated within the GIBBON toolbox. The mesh density was biased based on proximity to the bones.

Constitutive Modeling

The bulk soft tissue, the patellar ligament, and the liner are modeled as homogeneous materials. The socket is allowed to be spatially varying in mechanical behavior and can therefore be heterogeneous, i.e. each element may have different desired constitutive parameters. The non-linear elastic behavior of all materials is modeled using the following isotropic, and coupled hyperelastic strain energy density function [59]:

$$\psi = \frac{c}{m^2}\left(\sum_{i=1}^{3}(\lambda_i^m + \lambda_i^{-m} - 2)\right) + \frac{\kappa'}{2}(J - 1)^2 \tag{1}$$

The material parameters c and k' have units of stress and define a shear-modulus like and bulk-modulus like parameter respectively. The unitless parameter m sets the degree of non-linearity. Finally $\lambda_i$ are the principal stretches, and j is the volume ratio (determinant of the deformation gradient tensor). The constitutive parameters used are listed in Table 1. For the bulk soft tissue, the parameters were identified from dedicated subject-specific indentation tests (see our recent study [54]). FIG. 5A shows the custom designed and computer controlled indentation system (see also [60] and [61]). The system features a circular arrangement of indentors (square indentor heads 20×20 mm) which are used to record indentation force, time, and displacement data for multiple sites across the residuum. MRI was used for FEA model construction and MRI markers (FIG. 7B) served to co-locate the indentation locations. The experiments were simulated using dedicated inverse FEA (FIG. 7C). During inverse FEA constitutive parameters for the subject were determined by minimizing the difference between simulated and experimental boundary conditions for a combination of indentation locations. FIG. 7D shows a typical force-time curve for the experiment and FEA simulation following optimization, demonstrating the predictive capabilities of the biomechanical model (in our study [54] viscoelastic behaviour is also evaluated based on an expansion of the above formulation. However, the particular embodiment described here features only quasi-static evaluation, hence only the non-linear elastic parameters are considered).

As is common for constitutive modeling of soft tissue, in Sengeh et al. 2016 [54] near incompressibility was assumed by using the equivalent of k'=100·c. However, since in our former study no tissue deformation or shape changes were recorded, the degree of compressibility of the tissue was not sufficiently validated. Further, residual limbs are known to be capable of changing volume due to loading and with use of sockets, across different time scales [62], [63]. Therefore to allow for realistic pressures and deformations k'=18·c was used here, which does allow for some volume change of the tissue. For the subject included in this study a cast of the limb while pressurized at 90 kPa was available. Using FEA and the above parameters the response to such a pressure could also be simulated. The value for k' to use in the current study was estimated by altering it such that a similar degree of pressure induced skin displacement was qualitatively observed. For the patellar ligament the parameters were based on literature data for tensile testing of human patellar ligament tissue [64] (the reported linear elastic Young's modulus E=660 MPa was used to set $$c = \frac{E}{3}$$

and m=2). The patellar ligament, liner and socket materials were made relatively incompressible by setting k'=100·c. For the liner and socket materials the parameters were identified using uniaxial compression experiments (data not shown). For rigid regions the stiffest available material was used with c=1558 MPa. For compliant regions a spatial variation of socket materials is proposed which depends on the choice of design variation. As listed in Table 1, 5 different compliant materials are used here (with reported Shore A values of 27, 40, 50, 60 and 70).

TABLE 1

| | c [MPa] | m [·] | K' [MPa] |
|---|---|---|---|
| Bulk soft tissue | $5.2 \cdot 10^{-3}$ | 4.74 | 18 · c |
| Patellar ligament | 220 | 2 | 100 · c |
| Liner | 0.113 | 4.57 | 100 · c |
| Socket rigid | 1558 | 2 | 100 · c |
| Socket compliant 1 | 1.18 | 2 | 100 · c |

TABLE 1-continued

|  | c [MPa] | m [·] | K' [MPa] |
|---|---|---|---|
| Socket compliant 2 | 1.62 | 2 | 100 · c |
| Socket compliant 3 | 2.04 | 2 | 100 · c |
| Socket compliant 4 | 2.8 | 2 | 100 · c |
| Socket compliant 5 | 3.59 | 2 | 100 · c |

Controlling Design Features

The liner fitting pressure was set at a homogeneous 90 kPa. This pressure was manually determined by varying it until the mean skin surface pressure was qualitatively observed to be approximately 15 kPa, which was deemed a target donned liner skin surface pressure. For the sockets a more complex procedure is followed. A design map is defined, denoted by $\mathcal{D}$, with $\mathcal{D} \in [0\ 1]$, which can be used to set the local socket fitting pressure and local socket element stiffness through a linear mapping. The spatially varying fitting pressures $\mathcal{P}$ for each triangular skin surface element can be determined using:

$$\mathcal{P} = p_{min} + \mathcal{D}\,(p_{max} - p_{min}) \tag{2}$$

Here $p_{max}$ and $p_{min}$ are the desired minimum and maximum fitting pressures. For the spatially varying mechanical properties of the socket the constitutive parameters c for each socket element $\mathcal{C}$ can then be derived from:

$$\mathcal{C} = c_{min} \mathcal{D}\,(c_{max} - c_{min}) \tag{3}$$

Here $c_{max}$ and $c_{min}$ are the desired minimum and maximum c values. In principle the constitutive parameters can be continuously varied between the minimum and maximum level allowing for the creating of smooth parameter variations. However, as mentioned before, for the current 3D printer only 5 compliant material types are available (see Table 1). By using the design map, the spatial variation of fitting pressure and socket material parameters can each be controlled with two parameters (a desired minimum and a maximum). For iterative design optimization procedures, the design map $\mathcal{D}$ can be made to evolve with each iteration and a different design map can be employed for the fitting pressure and the socket materials.

For the traditional artisanal approach, the socket source geometry (plaster mold) is used to inform the designs, and local shape adjustments are made manually based on knowledge of safe and unsafe regions. These regions are largely identified using palpation of the subject's limb. FIGS. 8A-8B show typically reported vulnerable and safe regions for loading (see also: [35]). Since palpation assesses a combination of local tissue stiffness and thickness (i.e. distance to bones). This assessment is here termed "displaceability", i.e. the ability of the tissue to locally deform when loaded. A prosthetists design map is therefore based on experience and palpation. To create an automated assessment of displaceability FEA is used here. Displaceability is computed as the magnitude of skin surface displacement following the application of a homogenous pressure of 90 kPa (i.e. the response to the liner fitting pressure is used here). FIG. 8C shows FEA derived relative displaceability data (normalized total displacement).

Reported vulnerable and safe regions are seen to correlate well with regions with low and high displaceability respectively. FIG. 8D shows that the displaceability data can also be mapped onto the socket elements (based on nearest neighbor interpolation). This mapped data can be used as a displaceability based design map to control socket design features. However, although this data appears informative most of the safe and vulnerable regions it does not sufficiently highlight the patellar ligament region which is generally deemed safe for loading. The region at the patellar ligament (marked with a white ellipse in FIG. 8D) was therefore enhanced. The design map in FIG. 8D is denoted $\mathcal{D}_{123}$. FIG. 8E is a variation of this design map where the design map was reduced for elements close to the fibular head and distal end of the tibia. This reduction was informed by the fact that high pressures are observed here for simulations with the mapping $\mathcal{D}_{123}$. This adjusted design map is denoted $\mathcal{D}_4$, and can be viewed as the result of one manual design optimization iteration with respect to the mapping $\mathcal{D}_{123}$. Both design maps have also been nulled at the cut-line rim (10 mm high) to create a comfortable rim (as nulled regions result in compliant materials and low fitting pressures).

In order to study the effect of the socket shape (controlled by fitting pressures) and material properties, 4 different design strategies are evaluated: 1) a rigid socket designed using a homogeneous fitting pressure, 2) a rigid socket designed using a spatially varying fitting pressure, 3) a compliant socket designed using a spatially varying fitting pressure and featuring spatially varying socket stiffness, 4) the same as 3 but with added soft features over the distal end and fibular head. In terms of fitting pressures, the concept of approach 1 is comparable to a total surface bearing (TSB) design, while approaches 2-4 are comparable to a patellar tendon bearing (PTB) design (see also [65]). The parameters used for these design variations are listed in Table 2. A visualization of the resulting socket material and fitting pressure distributions is shown in FIGS. 9A-9D. The rigid material regions in all designs are fully supported during FEA. For the compliant designs (variation 3 and 4) the rigid material is employed where the design map is >0.25. These regions are highlighted in red in the material visualizations of FIGS. 9A-9D (and are to be bonded to a rigid external socket). The compliant materials are then linearly mapped for the remaining unsupported regions. The fitting pressures are nulled at the rims and have one further adjustment for the spatially varying pressure designs; the fitting pressure at the patellar ligament (a load safe region) is further enhanced by multiplying the fitting pressure suggested by the map by a factor $f_{pat}$ (Table 2).

TABLE 2

| Design strategy | $\{c_{min}, c_{max}\}$ [MPa] | $\{p_{min}, p_{max}\}$ [kPa] | $f_{pat}$ | Mapping |
|---|---|---|---|---|
| 1 | {1558, 1558} | {60.3, 60.3} | 1 | $\mathcal{D}_{123}$ |
| 2 | {1558, 1558} | {30, 69} | 6 | $\mathcal{D}_{123}$ |
| 3 | {1.18, 1558} | {30, 74} | 6 | $\mathcal{D}_{123}$ |
| 4 | {1.18, 1558} | {30, 84.8} | 6 | $\mathcal{D}_4$ |

FEA Based Design and Evaluation

The FEA based design and evaluation procedure consists of 5 steps which are schematically illustrated in FIG. 10. During all steps the bone nodes were rigidly supported and therefore constrained from moving. In addition, the nodes of the top surface of the model were constrained from moving in the z-direction (but free to move in the x- and y-directions). The socket, liner, and tissue regions share nodes at each interface, simulating high friction tied interfaces. The liner and socket are each designed and donned in separate 2 step procedures. First fitting pressures are used to morph the geometries into desired designs. During the design phase the liner and socket are in a "ghosted" form i.e. they do not have significant stiffness and develop no significant stresses (hence shown as transparent in FIG. 10). Once their desired design is achieved they are assigned with natural mechanical properties in a stress free state. This process of morphing the designs (while the soft tissue is pre-loaded) without developing stresses in the liner or socket regions is achieved by modeling the liner and socket materials as multi-generational materials (see [47]). The liner and socket parameter $c$ is made generation dependent in the following way:

$$c = \begin{cases} \dfrac{c_{soft}}{1000} & \gamma = 1 \\ c_{true} & \gamma = 2 \end{cases} \tag{4}$$

Where $\gamma$ is a generation index (see also FIG. 10), $c_{soft}$ denotes the c parameter for soft tissue, and $c_{true}$ denotes the true (physically realistic) c parameter. Since during the design phase the material can be made to have negligible stiffness ($\gamma=1$) they remain in an effectively stress free state when the source geometry is morphed into a desired design. However, critically during this deformation, the soft tissue is pre-loaded and does build up material stresses. Hence effectively the multi-generational approach is used here to allow for the "switching off" of the liner and socket material properties during FEA based morphing, and the subsequent "switching on" of the liner and socket materials in a stress free state when the desired shape is obtained. Once the liner or socket are designed by the fitting pressures and in their second generation ($\gamma=2$) they are able to develop stresses. The use of multi-generation materials in this way therefore forms a simple means of driving the designs of the liner and socket and simultaneously provides a means to simulate the pre-loading induced by donning.

In step 1 only the soft tissues are developing significant stresses ($\gamma_{liner}=1$, $\gamma_{socket}=1$), liner fitting pressures are applied loading and deforming the limb and freely morphing and carrying the liner source geometry with it to it's desired design. In step (2) the liner material is assigned with its natural mechanical properties ($\gamma_{liner}=2$, $\gamma_{socket}=1$). The liner starts out stress free in its equilibrium shape but, as the liner fitting pressures are ramped down, the tissue experiences some relaxation and starts to push against the liner, deforming it until the tissue and liner reach equilibrium. Steps 1 and 2 therefore function to design and don the liner. During steps 1 and 2 the socket source geometry remained in its ghosted form, bonded to the liner and was carried along with it. In step 3 only the liner and soft tissues are able to develop significant stresses ($\gamma_{liner}=2$, $\gamma_{socket}=1$) and the socket fitting pressures are applied to the skin surface. The socket fitting pressures deform the limb and the liner, and morph and carry the socket to its desired design. In step 4 the socket material is assigned with its natural (and potentially spatially varying) mechanical properties ($\gamma_{liner}=2$, $\gamma_{socket}=2$) The socket starts out stress free in its equilibrium shape but, as the socket fitting pressures are ramped down, the tissue experiences some relaxation and starts to push against the liner and socket, deforming both until the tissue, liner and socket reach equilibrium. Steps (3) and (4) therefore function to design and don the socket. Finally, in step (5) the supported socket nodes are moved upward by 3 mm. Displacement controlled simulations are used and the fitting pressures listed in Table 2 were iteratively adjusted until the reaction force was 765.18±2N (the force due to body weight). Once the 5 step FEA procedure is completed tissue loading measures indicative of tissue comfort or injury risk can be studied and final stresses and strains are output to derive skin surface pressure and tissue maximum shear strains.

Results

Image-Based Modeling and Data-Driven Liner and Socket Design

FIGS. 3A-3K illustrate the data-driven and automated design and computational modeling framework for development of subject-specific sockets and liners. For FEA the computational time for design and evaluation is currently 12 minutes (32Gb RAM, Intel Core i7-4910MQ CPU). Given this computational speed it is feasible to do iterative FEA based design optimization. The outcome of the framework is a set of CAD files allowing for computer aided manufacture. FIGS. 11A-11F and FIGS. 12A-12E illustrate production of liner and socket designs.

The FEA procedure can be used to generate and export an optimal socket design (FIG. 12A and FIG. 3J). For socket evaluation this design can be 3D printed (FIG. 12B) (e.g. by varying concentrations of the soft Shore 27 TangoBlack and rigid VeroWhite material with an Objet500 Connex 3D printer, Stratasys Ltd., Eden Prairie, Minnesota, USA). For support a rigid outer socket can be automatically defined (FIG. 12C). This outer socket can be 3D printed as well (FIG. 12D) and is offset where the inner socket is compliant to allow for deformation. The outer socket also contains an additional base feature (automatically created) to connect to a foot/ankle system. FIG. 12E shows the complete system with a sleeve used for suspension.

FEA Based Evaluation of Subject-Specific Socket Design Strategies

To evaluate this embodiment a single liner design is explored and 4 socket design strategies are compared: Design 1 is a rigid socket with a constant fitting pressure, design 2 is a rigid socket with a spatially varying fitting pressure, design 3 is a compliant socket with a spatially varying fitting pressure, design 4 is the same as design 3 but with reduced fitting pressure and socket material stiffness at the fibular head and the distal end of the tibia where high pressures were observed. FIGS. 13A-13D, and FIGS. 14A-14D, show the outcomes of the 4 socket design variations after body weight loading in terms of skin surface pressures and maximum shear (Green-Lagrange) shear strain, respectively.

Discussion

The invention is a method and system for the quantitative design, and computational evaluation, of a person-specific mechanical interface between a device and a human biological segment. Examples are provided for the design of a prosthetic socket interface including liner, inner socket and outer socket components. An overview of the steps of the method presented in FIGS. 3A-3K and includes: imaging to accurately record tissue geometries; and indentation testing for tissue biomechanical behavior analysis; FEA model development informed by the subject-specific imaging and indentation data; FEA-based design and optimization to predict liner and socket equilibrium shape and impedances, and the ability to export derived CAD files for the liner and socket for 3D printing based manufacture of the compliant and spatially varying stiffness designs. The entire design process is automated and driven by subject-specific features. The design is generated and evaluated using FEA. Evaluation is based on analysis of tissue loading during simulated standing, i.e. the application of a force equivalent to body weight.

The method can include the steps of obtaining a subject-specific geometry by segmenting MRI data; using anatomical landmarks to automatically create the socket cut-lines; offsetting liner and socket source geometries from the skin surface meshing them with the soft tissue to form a FEA model; assigning indentation-derived tissue mechanical properties; defining spatially varying design features, such as socket compliance and fitting pressure, using FEA-based measures of tissue vulnerability; fitting pressure fields, by morphing the liner and socket into their desired shape, while also donning to pre-load the tissue donning; and evaluating the designs for body weight loading; and exporting optimal designs resulting from the method for 3D printing based manufacturing.

Since FEA-based design and design evaluation can, in some instances, take place in about twelve minutes, the framework opens the door to iterative FEA-based socket and liner design optimization. For optimization, the design controlling parameters can be updated in an iterative fashion while minimizing measures predictive of comfort, such as skin contact pressure and tissue strain. This process is illustrated by the circular process in FIGS. 3A-3K labelled "Virtual test socket optimization."

In order to study the effect of the socket shape (controlled by fitting pressures) and material properties, 4 different design strategies are evaluated: 1) a rigid socket designed using a homogeneous fitting pressure, 2) a rigid socket designed using a spatially varying fitting pressure, 3) a compliant socket designed using a spatially varying fitting pressure and featuring spatially varying socket stiffness, 4) the same as 3 but with reduced fitting pressures and socket material stiffness over the distal end and fibular head. Following body weight loading these approaches have varying outcomes in terms of skin surface pressure and tissue maximum shear strain, as shown in FIGS. 13A-13D and FIGS. 14A-14D, respectively.

From FIGS. 13A-13D it can be observed that a rigid socket design based on a homogeneous socket fitting pressure (design 1) presents with high pressures (close to 100 kPa) at many known vulnerable regions such as the distal end of the tibia, the front of the tibia and the fibular head. By instead using a spatially varying fitting pressure (design 2) the pressure can be enhanced at safe regions such as the patellar ligament and the calf region. Through these enhancements, relief is obtained for the front of the tibia and the top of the fibular head. However, high pressures remain at the lower portion of the fibular head and the region close to the distal end of the tibia. By utilizing not only spatially varying fitting pressures but also compliant materials such as in design 3, the contact pressure at the front of the tibia can be further reduced. However, high pressures remain at the lower part of the fibular head and at the distal end of the limb. If based on these findings the socket material stiffness and fitting pressures are reduced further for these regions (design 4), these observed pressures can be reduced. These results show the possible benefit, in terms of skin contact pressure, of enhancing loading at safe regions while reducing loading at vulnerable regions. Further, these results show that skin contact pressures can greatly, and selectively, be reduced by incorporating deformable and soft socket materials at vulnerable regions.

FIGS. 14A-14D show slice views highlighting the maximum shear strains at the tibia and fibula for the 4 design variations. For the rigid socket defined by a homogeneous pressure (design 1) maximum shear strains in excess of 0.5 are observed at the distal end of the tibia, the fibular head and the distal end of the fibula. If instead a spatially varying driving pressure is used (design 2) some of the load-safe regions are loaded more increasing deformations in these safe regions. Although the maximum shear strain at the fibular head remains 0.5, a reduction to 0.4 is seen at the distal end of the tibia and fibula. The pattern remains similar for design 3 where compliant materials are employed, although the strains are reduced at the front of the tibia. Design 4 presents with a similar pattern; however, the reduced fitting pressures and socket stiffness distally have further reduced maximum shear strains at the fibular head and distal end.

Variations of the method of the invention can be practiced that deviate from the presented embodiments. In the presented embodiments, the FEA procedures assume isotropic, and hyperelastic constitutive behavior for the soft tissues and engineering materials (socket and liner). In addition, the soft tissues are modeled as two regions only, the patellar tendon, and a grouped soft tissue region representing skin, adipose and muscle tissue. Also, a multi-layered material structure, including a skin and adipose tissue layer, can be modeled. In addition, the biological materials can be represented using more realistic viscoelastic (e.g. biphasic) material formulations. In addition, anisotropy of tissues such as tendon and muscle can be incorporated through the use of material formulations with fibrous reinforcement. Such formulations require input from additional experimental measurements to inform the material fiber directions. For muscle and tendon, the MM acquisitions can be expanded to include measurements such as Diffusion Tensor MRI [66]. From such data the local fiber direction can be set for each FEA element. The non-linear elastic, viscoelastic and anisotropic material parameters can be derived from dedicated mechanical experiments, such as MM-based indentation experiments [67]. In addition, it is possible to implement stiffness estimates directly from elastography techniques, e.g. based on MM (e.g. [68]) or ultrasound.

Further, in the specific embodiments presented herein, the bones are modeled as rigid voids that are fixed in space. In addition, the patellar bone is not bonded to these bones. As such, the residual limb simulation modeling could tie the tendon to the bones and allow for relative motion between the bones.

In certain embodiments, the source geometries for the liner and socket are based on offsetting of the undeformed skin geometry. The geometry for the upper boundary (cut-lines) of the socket source geometry is defined by a set of anatomical landmarks. Through this approach, the source design of both the liner and socket are fully subject-data driven. However, other means to specify these designs could be employed. For example, the source geometries for the liner and socket could be based upon offsetting of the deformed skin geometry, using for example a skin deformation caused by a constant pressure loading. Still further, the liner and socket cut-lines could be informed by measurements of blood flow and nerve transduction under loading in addition to the presented anatomical landmark design methodology.

In certain embodiments, displaceability (local skin displacement magnitude in response to a homogeneous pressure) is used to linearly define the driving pressures that are used in the morphing process of the source geometries for the liner and socket. Regions with high displaceability are assumed to correspond to safe regions where relatively high pressures can be applied without causing discomfort. In distinction, regions with low displaceability are assumed to correspond to unsafe regions where relatively low pressures must be applied. Although the presented functional relationship between displaceability and driving pressures allows for subject-data driven design of the socket, there are some possible variations that fall within the general framework of the invention. For instance, the map could consider the direction of displacement, or consider alternative load orientations. In addition, the map could capture nerves and other vulnerable features that may significantly impact comfort. As such, at present some of the socket features have been altered with respect to the displaceability map, i.e. the size of the soft regions near the fibular head and distal end of the tibia have been increased. Although these enhancements have been linked to local anatomy (based on proximity to bony landmarks), they are at present "experience based." Therefore, in alterative embodiments, the subject-specific recordings that drive the design, could also address these regions in more detail, and could inform on size of features, the orientation of loading, and on the presence of anatomical vulnerabilities such as nerves. The latter may be detectable from the non-invasive image data. However, if nerves follow predictable paths they may also be definable in terms of other anatomical features such as bony landmarks. The design can also be informed by separate dedicated loading experiments, such as indentation tests, allowing for the creation of local maximum displacement/load orientation maps (e.g. within an MRI scanner [67]).

In certain methods of the invention, the compliance of the inner socket is modulated by spatially varying its mechanical properties. At present the liner is defined as isotropic and homogeneous. However, spatially varying materials can also be explored for the liner. Further, through for instance the use of fiber reinforced materials, the use of anisotropic liner or socket materials may be pursued. The favored directions for such anisotropic materials can, for instance, potentially be related to local tissue deformation directions thereby offering anisotropic support/relief. In addition to spatial modulation of the elastic behavior of the materials, it is possible to spatially vary the thickness of at least one of the liner and the socket. The presented embodiments utilized constant thickness designs; however, expansion to spatially varying thickness designs based on subject-specific data can easily be realized and explored.

The method allows for iterative optimization of subject-specific mechanical interfaces. Optimization can be based on static loading, such as standing, however dynamic evaluations can also be performed. For example, the behavior of the mechanical interface can also be made temporally dependent on the current loading, such that the material or supporting structures alter stiffness and or pre-loading in response to assessed local loading using computer-controlled active materials with actuation.

FEA-based design generation and evaluation can employ additional empirical data than specifically presented herein. For instance, pressure sensors can be placed inside the socket (e.g. see [69]) and printable sensor designs have also been proposed (e.g. [70]). Motion capture systems can also be employed to study and capture dynamic loading data which may serve as input for load evaluation and validation. In addition, loading experiments can be conducted within an MRI scanner to allow for in-vivo deformation evaluation [71].

In certain embodiments, the presented FEA procedure features tied contact between the liner and skin surface. Although high friction is a common assumption it may be beneficial to allow for a sliding contact implementation, whereby a friction coefficient can be prescribed.

In certain embodiments, the elements used are 4-node tri-linear tetrahedral elements. More accurate results are obtainable using non-linear element formulations. For instance, 10-node quadratic tetrahedral elements can be used. In addition, mixed hexahedral and tetrahedral mesh formulations can be employed.

The liner and socket designs can be evaluated for static loading, i.e. body weight, along the length direction of the limb. However, during daily use the limb and socket are subjected to dynamic forces in excess of body weight and at varying orientations. It will be obvious to those of ordinary skill in the art that investigations of the socket designs can be employed for a wider array of load cases, such as dynamic loading in walking or running. The dynamic nature of the loading becomes especially important when tissue and printable material viscoelasticity are concerned.

MRI is a suitable modality for non-invasive imaging of soft tissue. Besides anatomical structure, it also offers methods to study dynamic soft tissue deformation (e.g. [71]), imaging of fibrous architecture (e.g. [66]), and also MR elastography based tissue stiffness assessment (e.g. [68]). Other non-invasive imaging techniques such as ultrasound can also be employed when practicing the invention presented herein. Both MRI and ultrasound offer internal anatomical structure. However, if these advanced medical imaging systems are too costly, it may be possible to use multi-orientation photography to create 3D models of the external geometry. This may then be combined with statistical shape modeling (e.g. based on a library of photography linked with MM based models) to generate 3D subject geometries with internal bone features.

The spatially varying features generally are controlled by a "map," in this case displaceability. This may be convenient since the entire spatial variation across thousands of tissue sites can be controlled using a reduced set of parameters. It is possible to freely vary the elastic parameters, however, and allow deviation from the mapping assumption. If this is combined with iterative FEA based optimization, however, this would lead to many unknowns (i.e. 1 or more parameters per element). In this case it may be more practical to create an iterative FEA optimization procedure that employs algorithms for the evolution of proposed stiffness changes from one iteration to the next. Local elastic behavior can for instance be made dependent on local tissue loading conditions, as well as temporal loading as seen in normal gait.

In another embodiment, shown in FIG. 15, the invention is a system for designing a biological body segment of a subject. System 10 includes modeler 14 that generates a quantitative model of the biological body segment from the subject-specific data 12. The subject-specific data 12 can include geometry of the biological body segment and may also include mechanical properties of the biological body segment. Analyzer 16 conducts a biophysical analysis to thereby establish a relationship (e.g., a functional relationship) between the quantitative model and at least one feature of a biomechanical interface contacting the biological body segment, the at least one feature being associated with physiological benefit of the biological body segment. Evaluator 18 applies the relationship to the at least one feature of the biomechanical interface contacting the biological body segment to thereby obtain design 20 for the biomechanical interface of the device.

REFERENCES

[1] K. Ziegler-Graham, E. J. MacKenzie, P. L. Ephraim, T. G. Travison, and R. Brookmeyer, "Estimating the Prevalence of Limb Loss in the United States: 2005 to 2050," *Arch. Phys. Med. Rehabil.*, vol. 89, no. 3, pp. 422-429, March 2008.

[2] C. Mauffrey and D. J. Hak, Eds., *Passport for the Orthopedic Boards and FRCS Examination.* Paris: Springer Paris, 2015.

[3] V. Y. Ma, L. Chan, and K. J. Carruthers, "Incidence, prevalence, costs, and impact on disability of common conditions requiring rehabilitation in the United States: stroke, spinal cord injury, traumatic brain injury, multiple sclerosis, osteoarthritis, rheumatoid arthritis, limb loss, and back pa," *Arch. Phys. Med. Rehabil.*, vol. 95, no. 5, p. 986-995. e1, May 2014.

[4] J. E. Kurichi, W. B. Vogel, P. L. Kwong, D. Xie, B. E. Bates, and M. G. Stineman, "Factors associated with total inpatient costs and length of stay during surgical hospitalization among veterans who underwent lower extremity amputation.," *Am. J. Phys. Med. Rehabil.*, vol. 92, no. 3, pp. 203-14, March 2013.

[5] H. M. Herr and a. M. Grabowski, "Bionic ankle-foot prosthesis normalizes walking gait for persons with leg amputation," *Proc. R. Soc. B Biol. Sci.*, vol. 279, no. 1728, pp. 457-464, February 2012.

[6] J. T. Kahle, "Conventional and Hydrostatic Transtibial Interface Comparison," *JPO J. Prosthetics Orthot.*, vol. 11, no. 4, pp. 85-91,1999.

[7] M. Muller, T. B. Staats, M. Leach, and I. Fothergill, "Total Surface Bearing Trans-Tibial Socket Design Impression Techniques."

[8] J. E. Sanders, E. L. Rogers, E. a Sorenson, G. S. Lee, and D. C. Abrahamson, "CAD/CAM transtibial prosthetic sockets from central fabrication facilities: how accurate are they?," *J. Rehabil. Res. Dev.*, vol. 44, no. 3, pp. 395-405,2007.

[9] L. E. Pezzin, T. R. Dillingham, E. J. MacKenzie, P. Ephraim, and P. Rossbach, "Use and satisfaction with prosthetic limb devices and related services," *Arch. Phys. Med. Rehabil.*, vol. 85, no. 5, pp. 723-729, May 2004.

[10] H. E. J. Meulenbelt, P. U. Dijkstra, M. F. Jonkman, and J. H. B. Geertzen, "Skin problems in lower limb amputees: a systematic review.," *Disabil. Rehabil.*, vol. 28, no. 10, pp. 603-608, May 2006.

[11] C. C. Lyon, J. Kulkarni, E. Zimerson, E. Van Ross, and M. H. Beck, "Skin disorders in amputees," *J. Am. Acad. Dermatol.*, vol. 42, no. 3, pp. 501-507, March 2000.

[12] M. B. Silver-Thorn, J. W. Steege, and D. S. Childress, "A review of prosthetic interface stress investigations.," *J. Rehabil. Res. Dev., vol.* 33, no. 3, pp. 253-266, July 1996.

[13] K. E. S. Buikema and J. H. Meyerle, "Amputation stump: Privileged harbor for infections, tumors, and immune disorders," *Clin. Dermatol.*, vol. 32, no. 5, pp. 670-677, January 2014.

[14] K. K. Ceelen, a. Stekelenburg, S. Loerakker, G. J. Strijkers, D. L. Bader, K. Nicolay, F. P. T. Baaijens, and C. W. J. Oomens, "Compression-induced damage and internal tissue strains are related," *J. Biomech.*, vol. 41, no. 16, pp. 3399-3404,2008.

[15] A. F. T. Mak, M. Zhang, and E. W. C. Tam, "Biomechanics of pressure ulcer in body tissues interacting with external forces during locomotion.," *Annu. Rev. Biomed. Eng.*, vol. 12, pp. 29-53, August 2010.

[16] M. Spittle, R. J. Collins, and H. Conner, "The incidence of pressure sores following lower limb amputations," *Pract. Diabetes Int.*, vol. 18, no. 2, pp. 57-61, March 2001.

[17] R. Gailey, K. Allen, J. Castles, J. Kucharik, and M. Roeder, "Review of secondary physical conditions associated with lower-limb amputation and long-term prosthesis use.," *J. Rehabil. Res. Dev.*, vol. 45, no. 1, pp. 15-29, January 2008.

[18] S. M. Tintle, J. J. Keeling, S. B. Shawen, J. A. Forsberg, and B. K. Potter, "Traumatic and trauma-related amputations: part I: general principles and lower-extremity amputations.," *J. Bone Joint Surg. Am.*, vol. 92, no. 17, pp. 2852-68, Decemeber 2010.

[19] M. C. Faustini, R. H. Crawford, R. R. Neptune, W. E. Rogers, and G. Bosker, "Design and analysis of orthogonally compliant features for local contact pressure relief in transtibial prostheses.," *J. Biomech. Eng., vol.* 127, no. 6, pp. 946-951,2005.

[20] B. Rogers, S. Stephens, A. Gitter, G. Bosker, and R. Crawford, "Double-Wall, Transtibial Prosthetic Socket Fabricated Using Selective Laser Sintering: A Case Study," *JPO J. Prosthetics Orthot.*, vol. 12, no. 3, pp. 97-103, November 2000.

[21] D. M. Sengeh and H. Herr, "A Variable-Impedance Prosthetic Socket for a Transtibial Amputee Designed from Magnetic Resonance Imaging Data," JPO J. Prosthetics Orthot., vol. 25, no. 3, pp. 129-137, July 2013.

[22] "BioSculptor Orthotic and Prosthetic CAD CAM Systems." [Online]. Available: http://www.biosculptor.com/. [Accessed: 6 May 2015].

[23] "Prosthetic CAD/CAM Systems by Infinity CAD Systems—Cost-effective, reliable and efficient system." [Online]. Available: http://www.infinitycadsystems.com/. [Accessed: 6 May 2015].

[24] "Vorum: Suppliers of CAD/CAM systems for P&O and Footware, and the creators of Canfit™ Design software." [Online]. Available: http://www.vorum.com/english/. [Accessed: 6 May 2015].

[25] "Orten-Accueil." [Online]. Available: http://www.orten.fr/. [Accessed: 6 May 2015].

[26] D. G. Smith and E. M. Burgess, "The use of CAD/CAM technology in prosthetics and orthotics—current clinical models and a view to the future.," *J. Rehabil. Res. Dev.*, vol. 38, no. 3, pp. 327-334, 2001.

[27] F. E. H. Tay, M. a. Manna, and L. X. Liu, "A CASD/CASM method for prosthetic socket fabrication using the FDM technology," *Rapid Prototyp. J.*, vol. 8, no. 4, pp. 258-262, 2002.

[28] Y. P. Zheng, a F. Mak, and a K. Leung, "State-of-the-art methods for geometric and biomechanical assessments of residual limbs: a review.," *J. Rehabil. Res. Dev.*, vol. 38, no. 5, pp. 487-504, 2001.

[29] T. Oberg, M. Lilja, T. Johansson, and A. Karsznia, "Clinical evaluation of trans-tibial prosthesis sockets: a comparison between CAD CAM and conventionally produced sockets.," *Prosthet. Orthot. Int.*, vol. 17, no. 3, pp. 164-171, 1993.

[30] J. E. Sanders, M. R. Severance, and K. J. Allyn, "Computer-socket manufacturing error: how much before it is clinically apparent?," *J. Rehabil. Res. Dev., vol.* 49, no. 4, pp. 567-82, January 2012.

[31] A. W. P. Buis, B. Condon, D. Brennan, B. McHugh, and D. Hadley, "Magnetic resonance imaging technology in transtibial socket research: a pilot study.," *J. Rehabil. Res. Dev.*, vol. 43, no. 7, pp. 883-890, January 2006.

[32] G. Colombo, G. Facoetti, C. Rizzi, A. Vitali, and A. Zanello, "Automatic 3D reconstruction of transfemoral residual limb from Mill images," in *Lecture Notes in Computer Science* (including subseries *Lecture Notes in Artificial Intelligence and Lecture Notes in Bioinformatics*), vol. 8026, no. PART 2, V. Duffy, Ed. Springer Berlin Heidelberg, 2013, pp. 324-332.

[33] T. Douglas, S. Solomonidis, W. Sandham, and W. Spence, "Ultrasound imaging in lower limb prosthetics," *IEEE Trans. Neural Syst. Rehabil. Eng.*, vol. 10, no. 1, pp. 11-21, 2002.

[34] D. Terzopoulos, "Computational Vision and Medical Image Processing," in *Computational Vision and Medical Image Processing: Recent Trends*, vol. 19, J. M. R. S.

Tavares and R. M. N. Jorge, Eds. Dordrecht: Springer Netherlands, 2011, pp. 125-143.

[35] G. Facoetti, S. Gabbiadini, G. Colombo, and C. Rizzi, "Knowledge-based system for guided modeling of sockets for lower limb prostheses," *Comput. Aided. Des. Appl.*, vol. 7, no. 5, pp. 723-737, August 2010.

[36] M. Buzzi, G. Colombo, G. Facoetti, S. Gabbiadini, and C. Rizzi, "3D modelling and knowledge: Tools to automate prosthesis development process," *Int. J. Interact. Des. Manuf.*, vol. 6, no. 1, pp. 41-53, January 2012.

[37] G. Colombo, G. Facoetti, D. Regazzoni, and C. Rizzi, "A full virtual approach to design and test lower limb prosthesis," *Virtual Phys. Prototyp.*, vol. 8, no. 2, pp. 97-111, June 2013.

[38] R. Morotti, C. Rizzi, D. Regazzoni, and G. Colombo, "Numerical Simulations and Experimental Data to Evaluate Residual Limb-Socket Interaction," in *Volume 3: Biomedical and Biotechnology Engineering*, 2014, p. V003T03A032.

[39] W. C. C. Lee and M. Zhang, "Using computational simulation to aid in the prediction of socket fit: A preliminary study," *Med. Eng. Phys.*, vol. 29, no. 8, pp. 923-929, October 2007.

[40] S. Portnoy, G. Yarnitzky, Z. Yizhar, a. Kristal, U. Oppenheim, I. Siev-Ner, and a. Gefen, "Real-time patient-specific finite element analysis of internal stresses in the soft tissues of a residual limb: A new tool for prosthetic fitting," *Ann. Biomed. Eng.*, vol. 35, no. 1, pp. 120-135, January 2007.

[41] C.-L. Wu, C.-H. Chang, A.-T. Hsu, C.-C. Lin, S.-I. Chen, and G.-L. Chang, "A proposal for the pre-evaluation protocol of below-knee socket design-integration pain tolerance with finite element analysis," *J. Chinese Inst. Eng., vol.* 26, no. 6, pp. 853-860, 2003.

[42] S. Portnoy, Z. Yizhar, N. Shabshin, Y. Itzchak, A. Kristal, Y. Dotan-Marom, I. Siev-Ner, and A. Gefen, "Internal mechanical conditions in the soft tissues of a residual limb of a trans-tibial amputee.," *J. Biomech.*, vol. 41, no. 9, pp. 1897-1909, January 2008.

[43] M. Zhang, M. Lord, a. R. Turner-Smith, and V. C. Roberts, "Development of a non-linear finite element modelling of the below-knee prosthetic socket interface," *Med. Eng. Phys.*, vol. 17, no. 8, pp. 559-566, December 1995.

[44] M. C. Faustini, R. R. Neptune, and R. H. Crawford, "The quasi-static response of compliant prosthetic sockets for transtibial amputees using finite element methods," *Med. Eng. Phys.*, vol. 28, no. 2, pp. 114-121, March 2006.

[45] W. C. C. Lee, M. Zhang, X. Jia, and J. T. M. Cheung, "Finite element modeling of the contact interface between trans-tibial residual limb and prosthetic socket," *Med. Eng. Phys.*, vol. 26, no. 8, pp. 655-662, October 2004.

[46] D. Lacroix and J. F. Ramirez Patiiio, "Finite element analysis of donning procedure of a prosthetic transfemoral socket," *Ann. Biomed. Eng.*, vol. 39, no. 12, pp. 2972-2983, December 2011.

[47] G. a. Ateshian and T. Ricken, "Multigenerational interstitial growth of biological tissues," *Biomech. Model. Mechanobiol.*, vol. 9, no. 6, pp. 689-702, December 2010.

[48] K. M. Moerman, "GIBBON (Hylobates Agilis)." 13 Oct. 2014.

[49] K. M. Moerman, A. J. Nederveen, and C. K. Simms, "Image Based Model Construction, Boundary Condition Specification and Inverse Fea Control: a Basic Matlab Toolkit for Febio," *Proc. 11th Int. Symp. Comput. Methods Biomech. Biomed. Eng.*, pp. 7-8,2013.

[50] S. A. Maas, B. J. Ellis, G. A. Ateshian, and J. A. Weiss, "FEBio: Finite Elements for Biomechanics," *J. Biomech. Eng.*, vol. 134, no. 1, p. 11005,2012.

[51] G. Holzapfel, *Nonlinear solid mechanics: A continuum approach for engineering.* John Wiley & Sons Ltd., 2000.

[52] J. Bonet and R. D. D. Wood, Nonlinear Continuum Mechanics for *Finite Element Analysis*. Cambridge University Press, 2008.

[53] M. Itskov, *Tensor Algebra and Tensor Analysis for Engineers (Table of Contents)*, 2nd ed. Springer, 2009.

[54] D. M. Sengeh, K. M. Moerman, A. Petron, and H. M. Herr, "Multi-material 3-D viscoelastic model of a transtibial residuum from in-vivo indentation and MRI data," *J. Mech. Behav. Biomed. Mater.*, vol. 59, pp. 379-392, February 2016.

[55] K. M. Moerman, D. M. Sengeh, and H. M. Herr, "Automated and Data-driven Computational Design of Patient-Specific Biomechanical Interfaces," *Open Sci. Framew.*, 2016.

[56] M. D. Robson, P. D. Gatehouse, M. Bydder, and G. M. Bydder, "Magnetic resonance: an introduction to ultrashort TE (UTE) imaging.," *Journal of computer assisted tomography*, 2003. [Online]. Available: http://www.ncbi.nlm.nih.gov/pubmed/14600447. [Accessed: 28 Apr. 2015].

[57] J. Vollmer, R. Mend, and H. Muller, "Improved Laplacian Smoothing of Noisy Surface Meshes," *Comput. Graph. Forum*, vol. 18, no. 3, pp. 131-138, 1999.

[58] H. Si, "TetGen, a Delaunay-Based Quality Tetrahedral Mesh Generator," *ACM Trans. Math. Softw., vol.* 41, no. 2, pp. 1-36, February 2015.

[59] K. M. Moerman, C. K. Simms, and T. Nagel, "Control of tension-compression asymmetry in Ogden hyperelasticity with application to soft tissue modelling," *J. Mech. Behav. Biomed. Mater.*, vol. 56, pp. 218-228, March 2016.

[60] H. M. Herr and A. Petron, "Physiological measurement device or wearable device interface simulator and method of use," 2013.

[61] A. Petron, J.-F. Duval, and H. Herr, "Multi-Indenter Device for in vivo Biomechanical Tissue Measurement," *IEEE Trans. Neural Syst. Rehabil. Eng.*, pp. 1-1, 2016.

[62] J. E. Sanders and S. Fatone, "Residual limb volume change: systematic review of measurement and management.," *J. Rehabil. Res. Dev.*, vol. 48, no. 8, pp. 949-86, 2011.

[63] S. G. Zachariah, R. Saxena, J. R. Fergason, and J. E. Sanders, "Shape and volume change in the transtibial residuum over the short term: preliminary investigation of six subjects.," *J. Rehabil. Res. Dev.*, vol. 41, no. 5, pp. 683-94, September 2004.

[64] G. A. Johnson, D. M. Tramaglini, R. E. Levine, K. Ohno, N. Y. Choi, and S. L. Y. Woo, "Tensile and viscoelastic properties of human patellar tendon.," *J. Orthop. Res., vol.* 12, no. 6, pp. 796-803, November 1994.

[65] S. R. Manucharian, "An Investigation of Comfort Level Trend Differences Between the Hands-On Patellar Tendon Bearing and Hands-Off Hydrocast Transtibial Prosthetic Sockets," *JPO J. Prosthetics Orthot.*, vol. 23, no. 3, pp. 124-140, 2011.

[66] M. Froeling, A. J. Nederveen, D. F. R. Heijtel, A. Lataster, C. Bos, K. Nicolay, M. Maas, M. R. Drost, and G. J. Strijkers, "Diffusion-tensor MRI reveals the complex muscle architecture of the human forearm," *J. Magn. Reson. Imaging*, vol. 36, no. 1, pp. 237-248, 2012.

[67] K. M. Moerman, A. M. J. Sprengers, A. J. Nederveen, and C. K. Simms, "A novel MRI compatible soft tissue indentor and fibre Bragg grating force sensor," *Med. Eng. Phys.*, vol. Article in, no. 4, pp. 486-499, April 2013.

[68] P. Garteiser, R. S. Sahebjavaher, L. C. Ter Beek, S. Salcudean, V. Vilgrain, B. E. Van Beers, and R. Sinkus, "Rapid acquisition of multifrequency, multislice and multidirectional MR elastography data with a fractionally encoded gradient echo sequence," *NMR Biomed.*, vol. 26, no. 10, pp. 1326-1335, May 2013.

[69] a. Schiff, R. Havey, G. Carandang, a. Wickman, J. Angelico, a. Patwardhan, and M. Pinzur, "Quantification of Shear Stresses Within a Transtibial Prosthetic Socket," *Foot Ankle Int.*, vol. 35, no. 8, pp. 779-782, May 2014.

[70] P. Laszczak, L. Jiang, D. L. Bader, D. Moser, and S. Zahedi, "Development and validation of a 3D-printed interfacial stress sensor for prosthetic applications," *Med. Eng. Phys., vol.* 37, no. 1, pp. 132-137, January 2015.

[71] K. M. Moerman, A. M. J. Sprengers, C. K. Simms, R. M. Lamerichs, J. Stoker, and A. J. Nederveen, "Validation of continuously tagged MRI for the measurement of dynamic 3D skeletal muscle tissue deformation," *Med. Phys.*, vol. 39, no. 4, p. 1793, April 2012.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for computer design and manufacture of a biomechanical interface of a wearable device interfacing an external surface of a biological body segment of a subject, comprising:

with a computer:

forming a quantitative model of the biological body segment from subject-specific data, the subject-specific data including geometry of the biological body segment;

conducting a biophysical analysis using the quantitative model of the biological body segment, the biophysical analysis including simulation of a response to a donning condition, the simulation including:

forming a single combined model using a finite element analysis (FEA) representation of the quantitative model of the biological body segment and an interface design, wherein the interface design is derived from and meshed with the quantitative model in order to simulate interaction between the quantitative model of the biological body segment and the interface design, the combined model comprising shared nodes, each of the shared nodes representing a portion of both the biological body segment model and the interface design, morphing the combined model in response to application of a fitting pressure, the morphing including adjusting an equilibrium shape of the interface design, assigning mechanical properties of the interface design to the morphed combined model, the assigning mechanical properties being generation dependent in the following way:

$$c = \begin{cases} \dfrac{c_{soft}}{1000} & \gamma = 1 \\ c_{true} & \gamma = 2 \end{cases}$$

wherein $\gamma$ is a generation index, $c_{soft}$ denotes the c parameter for soft tissue, and $c_{true}$ denotes a physically realistic c parameter, and decreasing the fitting pressure applied to the morphed combined model, the combined model responsively undergoing a relaxation phase, wherein following the relaxation phase, both the quantitative model of the biological body segment and the interface design components of the combined model are in a prestressed state to simulate the response to the donning condition, and exporting a final interface design for manufacture by a computer-controlled fabricator, the final interface design based on the morphed combined model.

2. The method of claim 1, wherein the biophysical analysis includes at least one member selected from the group of numerical methods consisting of finite element analysis, finite difference methods, finite volume methods, isogeometric analysis, boundary element methods, and meshfree methods.

3. The method of claim 1, further including optimizing at least one feature of the biomechanical interface for a physiological benefit of the biological body segment in the biomechanical interface by the biophysical analysis.

4. The method of claim 1, further including fabricating the biomechanical interface.

5. The method of claim 1, wherein the forming the quantitative model includes at least one non-invasive imaging method selected from the group consisting of magnetic resonance, x-ray, ultrasound, optical methods, tomography, thermography, and elastography, to form a non-invasive image.

6. The method of claim 5, including imaging tissue of the biological body segment.

7. The method of claim 5, wherein forming the quantitative model further includes employing the non-invasive imaging method to form an external tissue geometry and an internal tissue geometry of the biological body segment.

8. The method of claim 5, wherein forming the quantitative model includes employing the non-invasive imaging method to form an external tissue geometry and further includes statistical shape modeling to form an inferred internal geometry of the biological body segment.

9. The method of claim 1, wherein forming the quantitative model further includes performing a biomechanical material property analysis of the biological body segment.

10. The method of claim 9, wherein the biomechanical material property analysis includes a contact method.

11. The method of claim 10, wherein the contact method includes at least one method selected from the group consisting of indentation analysis, pressurization analysis, and vibration analysis.

12. The method of claim 9, wherein the biomechanical material property analysis includes a non-contact method.

13. The method of claim 12, wherein the non-contact method includes at least one method selected from the group consisting of ultrasound and magnetic resonance imaging.

14. The method of claim 13, wherein the non-contact method includes magnetic resonance elastography.

15. The method of claim 13, wherein the non-contact method includes ultrasound elastography.

16. The method of claim 9, wherein the biomechanical material property analysis includes analysis of at least one biomechanical property selected from the group consisting of impedance, damping, stiffness, the shear and bulk modulus (or any other stiffness or compliance tensor component), and other elastic, hyperelastic, viscoelastic, and poroelastic properties or constitutive parameters of the tissues.

17. The method of claim 16, wherein the at least one biomechanical property is mapped against the external tissue geometry.

18. A system for designing and manufacturing a biomechanical interface of a wearable device interfacing an external surface of a biological body segment of a subject, the system comprising:

a computer comprising:

a modeler that generates a quantitative model of the biological body segment from subject-specific data, the subject-specific data including geometry of the biological body segment;

an analyzer that conducts a biophysical analysis using the quantitative model of the biological body segment, the biophysical analysis including simulation of a response to a donning condition, the simulation including:

forming a single combined model using a finite element analysis FEA) representation of the quantitative model of the biological body segment and an interface design, wherein the interface design is derived from and meshed with the quantitative model, in order to simulate interaction between the quantitative model of the biological body segment and the interface design, the combined model comprising shared nodes, each of the shared nodes representing a portion of both the biological body segment model and the interface design such that the biological body segment model and the interface design are always tied together, morphing the combined model in response to a fitting pressure, the morphing including adjusting an equilibrium shape of the interface design, assigning mechanical properties of the interface design to the morphed combined model, the assigning mechanical properties being generation dependent in the following way:

$$c = \begin{cases} \dfrac{c_{soft}}{1000} & \gamma = 1 \\ c_{true} & \gamma = 2 \end{cases}$$

wherein $\gamma$ is a generation index, $c_{soft}$ denotes the c parameter for soft tissue, and $c_{true}$ denotes a physically realistic c parameter, and decreasing the fitting pressure applied to the morphed combined model, the combined model responsively undergoing a relaxation phase, wherein following the relaxation phase, both the quantitative model of the biological body segment and the interface design components of the combined model are in a pre-stressed state to simulate the response to the donning condition, an exporter that exports a final interface design for manufacture by a computer-controlled fabricator, the final interface design based on the morphed combined model.

19. The method of claim 1, wherein the biomechanical interface includes a liner and a socket, and wherein the final interface design is for the socket or the liner and socket.

20. The method of claim 1, wherein the biomechanical interface includes a liner and a socket, and wherein the donning condition includes liner donning induced pre-loads and socket donning induced pre-loads.

21. The method of claim 1, wherein conducting the biophysical analysis further comprises simulation of a response to a functional loading condition, the functional loading condition applied generally to the combined model along a length direction of the body segment to evaluate tissue loading expected during a functional use of the biomechanical interface.

22. The method of claim 21, wherein the method further comprises adjusting at least one feature of the biomechanical interface interfacing the biological body segment based on the response of the combined model to the functional loading condition to thereby obtain the final interface design for the biomechanical interface, the at least one feature associated with a physiological benefit of the biological body segment.

23. The system of claim 18, wherein conducting the biophysical analysis further comprises simulation of a response to a functional loading condition, the functional loading condition applied generally to the combined model along a length direction of the body segment to evaluate tissue loading expected during a functional use of the biomechanical interface.

24. The system of claim 23, wherein the system further comprises an evaluator that adjusts at least one feature of the biomechanical interface interfacing the biological body segment based on the response of the combined model to the functional loading condition to thereby obtain the final interface design for the biomechanical interface of the device, the at least one feature associated with a physiological benefit of the biological body segment.

25. The method of claim 1, wherein the morphing the combined model in response to application of a fitting pressure is performed before the assigning mechanical properties of the interface design to the morphed combined model.

26. The method of claim 25, wherein the assigning mechanical properties of the interface design to the morphed combined model is performed before the decreasing the fitting pressure applied to the morphed combined model.

27. The method of claim 26, wherein conducting the biophysical analysis further comprises simulation of a response to a functional loading condition, the functional loading condition applied generally to the combined model along a length direction of the body segment to evaluate tissue loading expected during a functional use of the biomechanical interface, wherein the decreasing the fitting pressure applied to the morphed combined model is performed before the simulation of a response to a functional loading condition.

28. The method of claim 1, further comprising applying a fitting pressure to the combined model when the interface design lacks mechanical strength such that the interface design is freely carried along with motion of the quantitative model of the biological body segment without developing stresses.

* * * * *